(12) United States Patent
Su et al.

(10) Patent No.: US 9,986,908 B2
(45) Date of Patent: Jun. 5, 2018

(54) MECHANICAL FEATURES OF AN EYE IMAGING APPARATUS

(71) Applicant: Visunex Medical Systems Co. Ltd., Grand Cayman, KY (US)

(72) Inventors: Wei Su, Sunnyvale, CA (US); Kang Lin, San Jose, CA (US)

(73) Assignee: VISUNEX MEDICAL SYSTEMS CO. LTD., Grand Cayman (KY)

( * ) Notice: Subject to any disclaimer, the term of this patent is extended or adjusted under 35 U.S.C. 154(b) by 0 days. days.

(21) Appl. No.: 14/312,590

(22) Filed: Jun. 23, 2014

(65) Prior Publication Data

US 2015/0366447 A1     Dec. 24, 2015

(51) Int. Cl.
| | |
|---|---|
| *A61B 3/12* | (2006.01) |
| *A61B 3/00* | (2006.01) |
| *A61B 3/14* | (2006.01) |

(52) U.S. Cl.
CPC .............. *A61B 3/12* (2013.01); *A61B 3/0008* (2013.01); *A61B 3/0016* (2013.01); *A61B 3/14* (2013.01)

(58) Field of Classification Search
CPC ........... A61B 3/00; A61B 3/0008; A61B 3/12; A61B 3/0016; A61B 5/14555
(Continued)

(56) References Cited

U.S. PATENT DOCUMENTS 3,301,627 A   1/1967 Kimura
3,373,864 A   3/1968 Barton et al.
(Continued)

FOREIGN PATENT DOCUMENTS

CN    1170343 A    1/1998
CN    101953675 A   1/2011
(Continued)

OTHER PUBLICATIONS

Su, Wei; U.S. Appl. No. 14/220,005 entitled "Eye Imaging Apparatus and Systems,," filed Mar. 19, 2014.
(Continued)

*Primary Examiner* — Darryl J Collins
*Assistant Examiner* — Journey Sumlar
(74) *Attorney, Agent, or Firm* — Arent Fox LLP

(57) ABSTRACT

Various embodiments of an eye imaging apparatus can be used to image the posterior and/or anterior portions of the eye. In some embodiments, the eye imaging apparatus can comprise a light source, imaging optics, an image sensor, and a handgrip comprising a bump shaped to fit with a palm of an operator. In some embodiments, the eye imaging apparatus can comprise a light source, imaging optics, an image sensor, and a control button. The control button can comprise a multi-functional button and/or a control button activated by the index finger. In some embodiments, the eye imaging apparatus can comprise a housing structure comprising a double shell structure with an inner shell and an outer shell, which can be configured to facilitate heat management. In some embodiments, the eye imaging apparatus can comprise a removable front imaging module, a main module, and an interconnect locking structure configured to enable repeated removal of the front imaging module from and re-attachment of the front imaging module to the main module. Various embodiments also comprise a carrying case for an eye imaging apparatus.

17 Claims, 17 Drawing Sheets

(58) Field of Classification Search
USPC .......................................... 351/206; 74/551.9
See application file for complete search history.

(56) References Cited

U.S. PATENT DOCUMENTS

| | | | |
|---|---|---|---|
| 3,944,341 A | 3/1976 | Pomerantzeff | |
| 4,023,189 A | 5/1977 | Govignon | |
| 4,026,638 A | 5/1977 | Govignon | |
| 4,357,088 A | 11/1982 | Pomerantzeff | |
| 4,461,551 A | 7/1984 | Blaha | |
| 5,036,446 A | 7/1991 | Quintanilla et al. | |
| 5,046,608 A | 9/1991 | Laipply | |
| 5,156,456 A | 10/1992 | Hoftman et al. | |
| 5,309,186 A | 5/1994 | Mizuno | |
| 5,343,861 A | 9/1994 | Herman | |
| 5,455,644 A | 10/1995 | Yazawa et al. | |
| 5,506,634 A | 4/1996 | Wei et al. | |
| 5,537,127 A * | 7/1996 | Jingu | A47B 21/00 248/921 |
| 5,537,162 A | 7/1996 | Hellmuth et al. | |
| 5,543,865 A | 8/1996 | Nanjo | |
| 5,608,472 A | 3/1997 | Szirth et al. | |
| 5,745,212 A | 4/1998 | Volk | |
| 5,751,396 A | 5/1998 | Masuda et al. | |
| 5,822,036 A | 10/1998 | Massie et al. | |
| 6,065,837 A | 5/2000 | Goldfain et al. | |
| 6,092,898 A | 7/2000 | De Juan, Jr. | |
| 6,267,752 B1 | 7/2001 | Svetliza | |
| 6,296,358 B1 | 10/2001 | Cornsweet et al. | |
| 6,305,804 B1 | 10/2001 | Rice et al. | |
| 6,361,167 B1 | 3/2002 | Su et al. | |
| 6,409,341 B1 | 6/2002 | Goldfain et al. | |
| 6,446,795 B1 | 9/2002 | Allen et al. | |
| 6,535,650 B1 | 3/2003 | Poulo et al. | |
| 6,636,696 B2 | 10/2003 | Saito | |
| 6,685,317 B2 | 2/2004 | Su et al. | |
| 6,761,455 B2 | 7/2004 | Sumiya | |
| 6,801,913 B2 | 10/2004 | Matsumura et al. | |
| 7,025,459 B2 | 4/2006 | Cornsweet et al. | |
| 7,048,379 B2 | 5/2006 | Miller et al. | |
| 7,147,329 B2 | 12/2006 | Stone et al. | |
| 7,156,518 B2 | 1/2007 | Cornsweet et al. | |
| 7,261,416 B2 | 8/2007 | Nishio et al. | |
| 7,306,336 B2 | 12/2007 | Akita et al. | |
| 7,347,553 B2 | 3/2008 | Matsumoto | |
| 7,357,248 B2 | 4/2008 | Sivakumar et al. | |
| 7,360,895 B2 | 4/2008 | Cornsweet et al. | |
| 7,387,385 B2 | 6/2008 | Sander | |
| 7,445,335 B2 | 11/2008 | Su et al. | |
| 7,448,753 B1 | 11/2008 | Chinnock | |
| 7,499,634 B2 | 3/2009 | Yogesan et al. | |
| 7,508,524 B2 | 3/2009 | Mahadevan-Jansen et al. | |
| 7,568,802 B2 | 8/2009 | Phinney et al. | |
| 7,621,636 B2 | 11/2009 | Su et al. | |
| 7,621,638 B2 | 11/2009 | Su et al. | |
| 7,650,064 B2 | 1/2010 | Isogai et al. | |
| 7,677,730 B2 | 3/2010 | Shimizu | |
| 7,731,361 B2 | 6/2010 | Honda | |
| 7,802,884 B2 | 9/2010 | Feldon et al. | |
| 7,815,310 B2 | 10/2010 | Su et al. | |
| 7,824,035 B2 | 11/2010 | Yamada et al. | |
| 7,854,510 B2 | 12/2010 | Verdooner et al. | |
| 7,986,859 B2 | 7/2011 | Fischer | |
| 8,002,410 B2 | 8/2011 | Shea | |
| 8,011,504 B1 | 9/2011 | Farberov | |
| 8,049,899 B2 | 11/2011 | Waelti et al. | |
| 8,064,989 B2 | 11/2011 | Brown et al. | |
| 8,103,061 B2 | 1/2012 | Payonk et al. | |
| 8,111,874 B2 | 2/2012 | Chan | |
| 8,115,830 B2 | 2/2012 | Kato et al. | |
| 8,118,431 B2 | 2/2012 | Shea et al. | |
| 8,237,805 B2 | 8/2012 | Nozaki | |
| 8,313,195 B2 | 11/2012 | Itoh et al. | |
| 8,328,356 B2 | 12/2012 | Cheng et al. | |
| 8,330,808 B2 | 12/2012 | Satake | |
| 8,356,900 B2 | 1/2013 | Zhou et al. | |
| 8,368,771 B2 | 2/2013 | Kino | |
| 8,421,855 B2 | 4/2013 | Buckland et al. | |
| 8,449,112 B2 | 5/2013 | Kishida | |
| 8,449,115 B2 | 5/2013 | Aikawa et al. | |
| 8,459,794 B2 | 6/2013 | Juhasz et al. | |
| 8,480,232 B2 | 7/2013 | Aikawa | |
| 8,506,082 B2 | 8/2013 | Saito | |
| 8,506,083 B2 | 8/2013 | Zhou et al. | |
| 8,518,109 B2 | 8/2013 | Shea et al. | |
| 8,550,650 B1 | 10/2013 | McGinty | |
| 8,561,135 B2 | 10/2013 | Upp | |
| 8,562,135 B2 | 10/2013 | Endo | |
| 8,594,757 B2 | 11/2013 | Boppart et al. | |
| 8,627,549 B2 * | 1/2014 | Vernieu | B29C 63/18 16/421 |
| 8,777,413 B2 | 7/2014 | Zhou et al. | |
| 8,811,745 B2 | 8/2014 | Farsiu et al. | |
| 8,820,929 B2 | 9/2014 | Shea et al. | |
| 8,820,931 B2 | 9/2014 | Walsh et al. | |
| 8,860,796 B2 | 10/2014 | Buckland et al. | |
| 8,861,061 B1 | 10/2014 | Graham et al. | |
| 8,896,842 B2 | 11/2014 | Bower et al. | |
| 8,926,350 B2 | 1/2015 | Wolfe et al. | |
| 8,955,971 B2 | 2/2015 | Ichikawa et al. | |
| 8,967,807 B2 | 3/2015 | Mizuno | |
| 9,022,568 B2 | 5/2015 | Shikaumi | |
| 9,022,569 B2 | 5/2015 | Nakahara et al. | |
| 9,106,831 B2 | 8/2015 | Miyamoto et al. | |
| 9,119,563 B2 | 9/2015 | Buckland et al. | |
| 9,149,179 B2 | 10/2015 | Barnard et al. | |
| 9,171,351 B2 | 10/2015 | Kita | |
| 9,211,064 B2 | 12/2015 | Wang | |
| 2001/0028438 A1 | 10/2001 | Matsumoto | |
| 2002/0097379 A1 | 7/2002 | Goldfain et al. | |
| 2002/0180727 A1 | 12/2002 | Guckenberger et al. | |
| 2003/0174211 A1 | 9/2003 | Imaoka et al. | |
| 2004/0118431 A1 | 6/2004 | Flynn | |
| 2005/0018135 A1 | 1/2005 | Maeda et al. | |
| 2005/0039565 A1 * | 2/2005 | Minkow | B62K 21/26 74/551.9 |
| 2005/0270484 A1 | 12/2005 | Maeda et al. | |
| 2005/0284774 A1 | 12/2005 | Mordaunt | |
| 2006/0114411 A1 | 6/2006 | Wei et al. | |
| 2006/0176447 A1 | 8/2006 | Reis | |
| 2006/0257138 A1 | 11/2006 | Fromm | |
| 2007/0188699 A1 | 8/2007 | Cech et al. | |
| 2007/0236663 A1 | 10/2007 | Waldorf et al. | |
| 2007/0244393 A1 | 10/2007 | Oshiki et al. | |
| 2008/0033371 A1 | 2/2008 | Updegraff et al. | |
| 2008/0071254 A1 | 3/2008 | Lummis et al. | |
| 2008/0211420 A1 | 9/2008 | Walker et al. | |
| 2009/0141237 A1 | 6/2009 | Izatt et al. | |
| 2009/0153797 A1 | 6/2009 | Allon et al. | |
| 2009/0185135 A1 | 7/2009 | Volk | |
| 2009/0211586 A1 | 8/2009 | Shea et al. | |
| 2010/0091244 A1 | 4/2010 | Volk | |
| 2010/0118270 A1 | 5/2010 | Shea et al. | |
| 2010/0149490 A1 | 6/2010 | Olivier et al. | |
| 2010/0184479 A1 | 7/2010 | Griffin | |
| 2010/0201604 A1 * | 8/2010 | Kee | G06F 1/1616 345/1.3 |
| 2010/0228236 A1 | 9/2010 | Muhlhoff et al. | |
| 2010/0253907 A1 | 10/2010 | Korb et al. | |
| 2010/0278394 A1 | 11/2010 | Raguin et al. | |
| 2011/0051086 A1 | 3/2011 | Takai et al. | |
| 2011/0052205 A1 | 3/2011 | Yu et al. | |
| 2011/0085137 A1 | 4/2011 | Kleen et al. | |
| 2011/0090460 A1 | 4/2011 | Graham et al. | |
| 2011/0103655 A1 | 5/2011 | Young et al. | |
| 2011/0176109 A1 * | 7/2011 | Mann | A61B 3/1208 351/206 |
| 2011/0234977 A1 | 9/2011 | Verdooner | |
| 2011/0267583 A1 | 11/2011 | Hayashi | |
| 2011/0299036 A1 * | 12/2011 | Goldenholz | A61B 3/1208 351/206 |
| 2012/0013140 A1 * | 1/2012 | Nitkin | A45C 13/22 294/153 |
| 2012/0026461 A1 | 2/2012 | Chou et al. | |

(56) References Cited

U.S. PATENT DOCUMENTS

| | | |
|---|---|---|
| 2012/0050683 A1 | 3/2012 | Yates |
| 2012/0092619 A1 | 4/2012 | Rowe |
| 2012/0099077 A1 | 4/2012 | Abt |
| 2012/0138503 A1 | 6/2012 | Patel |
| 2012/0162602 A1 | 6/2012 | Huening et al. |
| 2012/0224142 A1 | 9/2012 | Cornsweet et al. |
| 2012/0229617 A1 | 9/2012 | Yates et al. |
| 2012/0249748 A1 | 10/2012 | Nagano |
| 2012/0274900 A1 | 11/2012 | Horn et al. |
| 2012/0287255 A1 | 11/2012 | Ignatovich et al. |
| 2012/0300998 A1 | 11/2012 | Loudovski et al. |
| 2012/0320583 A1* | 12/2012 | Van Bommel .......... F21K 9/56 362/235 |
| 2013/0033593 A1 | 2/2013 | Chinnock et al. |
| 2013/0044200 A1 | 2/2013 | Brill et al. |
| 2013/0057828 A1 | 3/2013 | De Smet |
| 2013/0103014 A1 | 4/2013 | Gooding et al. |
| 2013/0135584 A1 | 5/2013 | Alasaarela et al. |
| 2013/0160621 A1* | 6/2013 | Marsden .......... B65D 83/0033 83/23 |
| 2013/0182895 A1 | 7/2013 | Touzov et al. |
| 2013/0235345 A1 | 9/2013 | Ohban |
| 2013/0261610 A1 | 10/2013 | LaConte et al. |
| 2013/0301003 A1 | 11/2013 | Wells et al. |
| 2013/0321906 A1 | 12/2013 | Kriofske et al. |
| 2014/0055749 A1 | 2/2014 | Zhou et al. |
| 2014/0063455 A1 | 3/2014 | Zhou et al. |
| 2014/0063456 A1 | 3/2014 | Zhou et al. |
| 2014/0063457 A1 | 3/2014 | Zhou et al. |
| 2014/0063459 A1 | 3/2014 | Zhou et al. |
| 2014/0063462 A1 | 3/2014 | Zhou et al. |
| 2014/0063463 A1 | 3/2014 | Zhou et al. |
| 2014/0078467 A1* | 3/2014 | Su ................ A61B 3/1208 351/207 |
| 2014/0085603 A1 | 3/2014 | Su et al. |
| 2014/0111768 A1 | 4/2014 | Komine |
| 2014/0125949 A1 | 5/2014 | Shea et al. |
| 2014/0152955 A1* | 6/2014 | Papageorgiou ...... G02B 25/002 351/159.52 |
| 2014/0221826 A1 | 8/2014 | Joos et al. |
| 2014/0226128 A1 | 8/2014 | Lawson et al. |
| 2014/0232987 A1 | 8/2014 | Westphal et al. |
| 2014/0268037 A1 | 9/2014 | Siminou |
| 2014/0293033 A1 | 10/2014 | Takii |
| 2014/0307226 A1 | 10/2014 | Lathrop et al. |
| 2014/0347628 A1 | 11/2014 | Martinez Corral et al. |
| 2014/0375952 A1 | 12/2014 | Hanebuchi |
| 2015/0335242 A1 | 11/2015 | Saito |
| 2016/0007850 A1 | 1/2016 | Su |
| 2016/0007956 A1* | 1/2016 | Mauldin, Jr. ........ A61B 8/0841 600/443 |
| 2016/0073877 A1 | 3/2016 | Su et al. |
| 2016/0073878 A1 | 3/2016 | Su et al. |
| 2016/0242734 A1 | 8/2016 | Su et al. |

FOREIGN PATENT DOCUMENTS

| | | |
|---|---|---|
| EP | 1289407 B1 | 12/2009 |
| EP | 2164383 A2 | 3/2010 |
| EP | 1928297 B1 | 11/2010 |
| EP | 2296531 A1 | 3/2011 |
| EP | 2312994 A2 | 4/2011 |
| EP | 2334222 A2 | 6/2011 |
| EP | 2066226 B1 | 12/2012 |
| EP | 2790570 A1 | 10/2014 |
| EP | 2845534 A1 | 3/2015 |
| JP | 2002238853 A | 8/2002 |
| TW | 201204314 A1 | 2/2012 |
| WO | WO03/057024 A1 | 7/2003 |
| WO | WO2006/013579 A1 | 2/2006 |
| WO | WO2010009450 A1 | 1/2010 |
| WO | WO2010/096756 A1 | 8/2010 |
| WO | WO2010/108228 A1 | 9/2010 |
| WO | WO2010117386 A1 | 10/2010 |
| WO | WO2011/022803 A1 | 3/2011 |
| WO | WO2012018991 A2 | 2/2012 |
| WO | WO2012/118907 A2 | 9/2012 |
| WO | WO2012118962 A2 | 9/2012 |
| WO | WO2012/154278 A1 | 11/2012 |
| WO | WO2013/020092 A1 | 2/2013 |
| WO | WO2013/059678 A1 | 4/2013 |
| WO | WO2013/162471 A1 | 10/2013 |
| WO | WO2013/165689 A1 | 11/2013 |
| WO | WO2013165614 A1 | 11/2013 |
| WO | WO2014/074573 A1 | 5/2014 |
| WO | WO2014/155403 A1 | 10/2014 |
| WO | WO2014/182769 A1 | 11/2014 |
| WO | WO2015/035175 A1 | 3/2015 |
| WO | WO2015/060897 A1 | 4/2015 |
| WO | WO2015/100294 A1 | 7/2015 |
| WO | WO2015/138963 A1 | 9/2015 |

OTHER PUBLICATIONS

Su, Wei; U.S. Appl. No. 14/191,291 entitled "Eye Imaging Apparatus With a Wide Field of View and Related Methods," filed Feb. 26, 2014.

American Academy of Ophthalmology; Vision Screening for Infants and Children (Policy Statement); American Association for Pediatric Ophthalmology and Strabismus; 3 pgs; © 2013 (earliest approval date: May 1991).

Cho et al.; Development of real-time dual-display handheld and bench-top hybrid-mode SD-OCTs; Sensors (Basel); 14(2); pp. 2171-2181; Jan. 27, 2014.

Device Optical; Kowa Genesis-D Hand Held Retinal Camera (product information); 3 pgs.; retrieved Jun. 23, 2014 from the Internet (http://www.deviceoptical.com/pd_kowa_genesisd.cfm).

Haddock et al; Simple, inexpensive technique for high-quality smartphone fundus photography in human and animal eyes; Journal of Ophthalmology; Hindawi Pub. Corp.; vol. 2013; Art. ID 518479; 5 pgs.; 2013 (accepted Aug. 18, 2013).

Su; U.S. Appl. No. 14/614,305 entitled "Eye imaging apparatus with a wide field of view and related methods," filed Feb. 4, 2015

Su; U.S. Appl. No. 15/007,101 entitled "Disposable cap for an eye imaging apparatus and related methods," filed Jan. 26, 2016.

Su; U.S. Appl. No. 14/881,070 entitled "Eye imaging apparatus with sequential illumination," filed Oct. 12, 2015.

Freebody; Reduced to the essentials—portable imaging gets high-tech; BioPhotonics; 13 pages; retrieved Jul. 13, 2016 from the internet at (http://www.photonics.com/Article.aspx?PID=1 &VID=127&IID=847&AID=57816).

Izatt et al.; Theory of optical coherence tomography; Optical Coherence Tomography; Springer berlin Heidelberg; pp. 47-72; (year of pub. sufficiently earlier than effective US filing date and any foreign priority date); 2008.

Ko; The angiovue difference; Optovue; OCT Angiography: The Newest Frontier for the Revolutionary Technology; Euro Times; 2014 supplement; pp. 1-2; Apr. 2014.

Koch; Optovue imaging device offers great potential for anterior segment imaging: The device's ability to image both the anterior and posterior cornea helps provide more accurate IOL calculations, among other things; Optovue; OCT Angiography: The Newest Frontier for the Revolutionary Technology; Euro Times; 2014 supplement; pp. 10-11; Apr. 2014.

Lumbroso; AngioVue Imaging System: The Future of Imaging? After evaluating this system, the answer is mostly likely 'yes'; Optovue; OCT Angiography: The Newest Frontier for the Revolutionary Technology; Euro Times; 2014 supplement; pp. 3-4; Apr. 2014.

Pavlis et al.; Optical differences between telescopes and microscopes; 5 pages; retrieved Jul. 13, 2016 from the internet at (http://www.microscopy-uk.org.uk/mag/imgjan10/mik-tele.pdf).

Puech; Imaging the optic disc with OCCT angiography: New optovue device enhances the way we view glaucoma patients; Optovue; OCT Angiography: The Newest Frontier for the Revolutionary Technology; Euro Times; 2014 supplement; pp. 8-9; Apr. 2014.

(56) References Cited

OTHER PUBLICATIONS

Ruggeri et al.; Imaging and full-length biometry of the eye during accommodation using spectral domain OCT with an optical switch, Biomedical Optics Express, 3(7); pp. 1506-1520; Jul. 6, 2012.
Staurenghi; Choroidal visualization using a non-invasive microvascular enhanced imaging platform; Optovue; OCT Angiography: The Newest Frontier for the Revolutionary Technology; Euro Times; 2014 supplement; pp. 5-6; Apr. 2014.
Su; U.S. Appl. No. 15/186,402 entitled "Wide field of view optical coherence tomography imaging system," filed Jun. 17, 2016.

\* cited by examiner

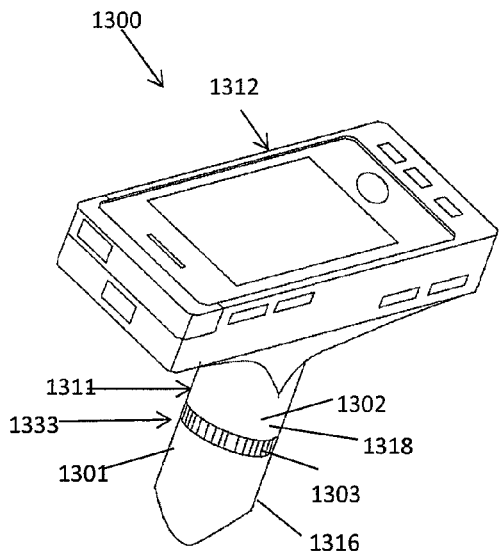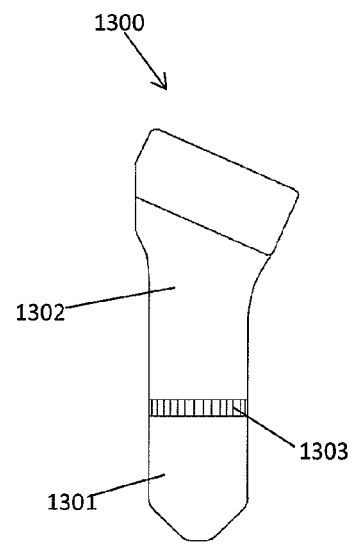
FIG. 13(A)    FIG. 13(B)
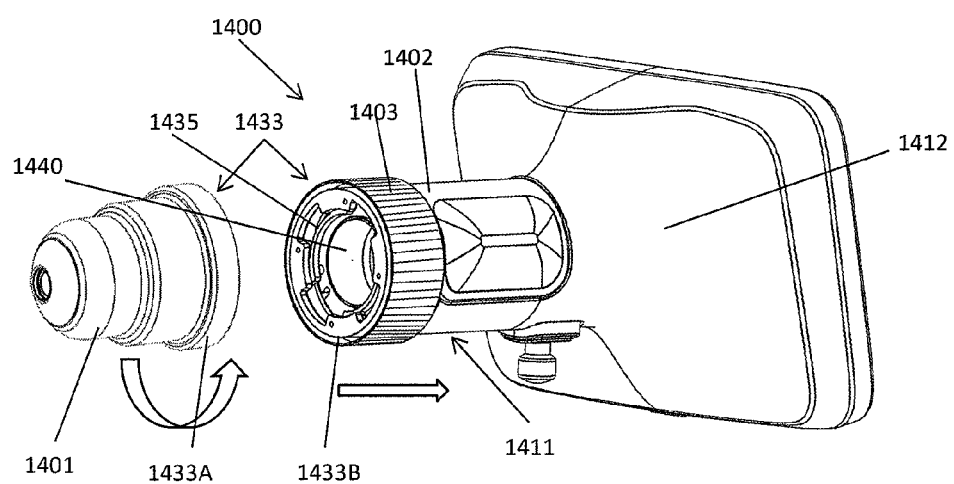
FIG. 14

MECHANICAL FEATURES OF AN EYE IMAGING APPARATUS

BACKGROUND

Field of the Invention

Various embodiments of the invention relate generally to an eye imaging apparatus, and particularly, the mechanical features of an eye imaging apparatus.

Description of the Related Art

Eyes are among the most valued human organs that play indispensable roles in life. Likewise, eye diseases and vision loss in general are serious problems. Moreover, eye diseases and vision problems among children, especially new-born babies, can have severe and far-reaching implications. For infants and small children, the visual centers in the brain are not fully mature. For the visual centers in the brain to develop properly, proper input from both eyes is desirable. Therefore good vision can be an important factor in the proper physical development and educational progress. Undetected eye problems in infants and others may result in irreversible loss of vision. Early detection and diagnosis provide the best opportunity for treatment and prevention of vision loss.

In eye examinations, eye imaging apparatus have become increasingly important. Conventional desk-top eye imaging apparatus are in general bulky and lack of mobility. Hand-held eye imaging apparatuses are more suitable for use in surgical rooms and in remote areas. However, the conventional hand-held apparatuses can be inconvenient to hold and perform alignment. In addition, heat dissipation can be a problem in the conventional hand-held imaging apparatus when the light sources are integrated in the apparatus.

SUMMARY OF VARIOUS EMBODIMENTS OF THE INVENTION

Various embodiments of the invention comprise an eye imaging apparatus comprising a light source configured to illuminate an eye, imaging optics configured to form an image of the eye, an image sensor disposed to receive said image of the eye, and a handgrip comprising a bump. The bump is shaped to fit with a palm of an operator holding the eye imaging apparatus.

In some embodiments, the handgrip comprises soft elastic material including plastic, rubber, rubber-like materials or combinations thereof. In some embodiments, the bump has a contact surface providing traction. In some embodiments the bump has a profile with a non-symmetric convex shape. The bump can have a profile substantially conforming to the shape of a portion of an ellipsoidal surface. The bump can be configured to have a maximum height of 60 mm or of 10 mm. The bump can have a length between about 20 mm and about 150 mm. The bump can have a width between about 5 mm to 40 mm.

In some embodiments, the handgrip is disposed on a portion of the imaging apparatus that houses at least a portion of the imaging optics. In some embodiments, the bump is configured to be adjustable. In some embodiments, the eye imaging apparatus further comprises a second bump, wherein the first bump is configured to for right-hand operation, and the second bump is configured to for left-hand operation.

In some embodiments, the handgrip further comprises a hollow ring, wherein the bump is attached to the hollow ring. The hollow ring can be removable and re attachable. In some embodiments, the handgrip is configured to be rotatable around a central axis of the handgrip.

In some embodiments, the handgrip comprises a partial ring structure, configured to be snapped-on to the imaging apparatus. The handgrip can be configured to be removable from the imaging apparatus, and be reattached to the imaging apparatus in a different direction.

In some embodiments, the eye imaging further comprises a multi-functional control button, wherein the multi-functional control button comprises a multi-functional and multi-directional button disposed on the housing, and wherein the multi-functional control button comprises electrical switches to control at least one of the light source and the image sensor. The imaging optics may comprise at least one lens positioned between the eye and the image sensor, wherein the lens is movable by an actuator; wherein the multi-functional control button further comprises electrical switches to the actuator of the lens. The handgrip may be configured to enable the operator to hold the imaging apparatus by using only four of five fingers of one hand, thus freeing an index finger to manipulate the multi-functional control button. The multi-functional control button may be positioned azimuthally at an angle of 90°, wherein the bump is rotatable from 270° to 360° for a right-handed operator and from 180° to 270° for a left-handed operator.

In some embodiments, the eye imaging apparatus comprises an exterior comprising a cylindrical portion, a cuboid portion and a transition portion between the cylindrical portion and the cuboid portion, wherein the transition portion has a profile configured to match the contour of the top side of a hand of an operator. In some embodiments, the eye imaging apparatus comprises a housing comprising a front removable module portion and a main module portion.

Various embodiments of the invention comprise an eye imaging apparatus comprising a light source configured to illuminate an eye, imaging optics configured to form an image of the eye, an image sensor disposed to receive said image of the eye, and a control button disposed for actuation by an index finger. The control button comprises one or more electrical switches configured control parameters of the eye imaging apparatus. In some embodiments, the control button comprises a joystick. In some embodiments, the control button comprises a multi-functional button. The multi-functional control button can be configured to control a least two of the light source, illumination optics, the imaging optics, the image sensor, and imaging processing.

In some embodiments, the eye imaging apparatus comprising the control button further comprises a handgrip comprising a bump. The bump can be shaped to substantially match with a contour of a palm of an operator holding the eye imaging apparatus. In some embodiments, the handgrip comprises soft material including plastic, rubber, rubber-like materials and combinations thereof. In some embodiments, the bump includes a contact surface that provides traction. In some embodiments, the bump has a profile with a non-symmetric convex shape. In some embodiments, the bump has a profile substantially confirming to the shape of a portion of an ellipsoid surface. In some embodiments, the bump is configured to have a maximum height of 60 mm. In some embodiments, the bump is configured to have a maximum height of 10 mm. In some embodiments, the bump has a length between about 20 mm and about 150 mm. In some embodiment, the bump has a width between about 5 mm to 40 mm. In some embodiments, the profile of the bump is further configured to match a contour of a thumb. In some embodiments the position of the bump is configured to be adjustable.

In some embodiments, the eye imaging apparatus further comprises a second bump, wherein the first bump is configured for right-hand operation, and the second bump is configured for left-hand operation. In some embodiments the handgrip further comprises a hollow ring, wherein the bump is attached to the hollow ring. The hollow ring can be removable and re-attachable. The handgrip can be configured to be rotatable around a central axis of the handgrip. In some embodiments, the handgrip comprises a partial ring structure, configured to be snapped-on to the imaging apparatus. The handgrip can be configured to be removable from the imaging apparatus, and be reattached to the imaging apparatus in a different direction.

In some embodiments, the handgrip is configured to enable the operator to hold the imaging apparatus by using only four of five fingers of one hand, thus freeing an index finger to manipulate the multi-functional control button. In some embodiments, the multi-functional control button is positioned azimuthally on the eye imaging apparatus at an angle 90°, wherein the bump is rotatable from 270° to 360° for a right-handed operator and from 180° to 270° for a left-handed operator.

In some embodiments, the eye imaging apparatus comprises an exterior comprising a cylindrical portion, a cuboid portion and a transition portion between the cylindrical portion and the cuboid portion, wherein the transition portion has a profile configured to match the contour of the top side of a hand of an operator. In some embodiments, the eye imaging apparatus comprises a housing comprising a front removable module portion and a main module portion. In some embodiments, the joy stick is configured to be tilted in a first direction and a second direction, and to be pushed inwards.

Various embodiments of the invention comprise an eye imaging apparatus comprising an exterior surface comprising a cylindrical portion, a cuboid portion, and a transition portion between the cylindrical portion and the cuboid portion. The eye imaging apparatus further comprises a light source to illuminate an eye; an image sensor to receive an image of the eye; at least one lens positioned between the eye and the image sensor; and a handgrip comprising a bump. The bump is shaped to fit with a palm of a hand of an operator, and the transition portion comprises contouring configured to match the top side of the hand.

In some embodiments, the eye imaging further comprises a multi-functional control button, wherein the multi-functional control button comprises a multi-directional button comprising electrical switches configured to control the light source and the image sensor. In some embodiments the handgrip is configured to enable the operator to hold the imaging apparatus by using only four of five fingers of one hand, thus freeing an index finger to manipulate the multi-functional control button. In some embodiments, the multi-functional control button is positioned azimuthally on said cylindrical portion at an angle of 90°, wherein the bump is rotatable from 270° to 360° for a right-handed operator and from 180° to 270° for a left-handed operator.

Various embodiments of the invention comprise a method to operate an eye imaging apparatus comprising: using three fingers including a middle finger, a ring finger and a pinky finger to hold a handgrip, using a thumb to secure the imaging apparatus, and using the index finger to operate a multi-functional control button. In some embodiments, the method further comprises selecting from a plurality of sizes a size of a handgrip that is compatible with the size of a hand of an operator. In some embodiments, the method further comprises sliding the handgrip onto a cylindrical portion of the eye imaging apparatus. In some embodiments, the method further comprises rotating the handgrip to a locked position.

Various embodiments of the invention comprise an eye imaging apparatus comprising an ergonomic exterior. The ergonomic exterior comprises a cylindrical portion, a cuboid portion and an ergonomic transition portion between the cylindrical portion and the cuboid portion. The eye imaging apparatus can further comprise a light source configured to illuminate an eye, imaging optics configured to form an image of the eye, an image sensor disposed to receive an image of the eye, and an ergonomic handgrip comprising an ergonomic bump.

Various embodiments of the invention comprise an eye imaging apparatus comprising a housing structure comprising a double shell structure. The double shell structure comprises an inner shell comprising a forward lens shell portion and a rearward lens shell portion; and an outer shell comprising a front portion and a back portion. The eye imaging apparatus can further comprise a light source in the housing to illuminate an eye, wherein the light source is disposed on a heat sink; and an image sensor disposed in the housing to receive an image of the eye.

In some embodiments, the light source and the heat sink are disposed in thermal contact with an outer surface of the inner shell. In some embodiments, the heat sink comprises a ring shaped structure. In some embodiments, the heat sink comprises ceramic, metal, or other thermal conductive material. In some embodiments, the inner shell comprises thermally conductive materials with a thermal conductivity higher than 10, 80, or 200 $W \cdot m^{-1} \cdot K^{-1}$. In some embodiments, the front portion of the outer shell comprises materials with relatively low thermal conductivity; wherein the back portion of the outer shell comprises materials with high thermal conductivity.

In some embodiments, an air gap or a thermal insulation material can be positioned between the heat sink and the front portion of the outer shell housing to reduce direct heat transfer. In some embodiments, a pair of large mating surfaces can be positioned between the forward lens shell and the rearward lens shell. In some embodiments, the eye imaging apparatus can further comprise an electronic device inside the housing and a heat pipe with a first end and a second end, wherein the first end of the heat pipe is in thermal contact with at a surface of the electronic device, and the second end is disposed at a surface of the housing.

Various embodiments of the invention comprise an eye imaging apparatus comprising a heat dissipation module. The heat dissipation module comprises a heat pipe with a first end and a second end, and a housing configured to be thermally conductive, wherein a portion of the housing comprises a large heat dissipation surface. The eye imaging apparatus can further comprise a light source configured to illuminate an eye, at least one electronic device producing thermal energy, and an image sensor disposed to receive an image of the eye, wherein the heat pipe is configured to conduct thermal energy away from said electronic device.

Various embodiments of the invention comprises an eye imaging apparatus comprising a removable front imaging module, a main module, and an interconnect locking structure. The interconnect locking structure can be configured to enable repeated removal of the front imaging module from the main module and repeated re-attachment of the front imaging module to the main module. The removable front imaging module can comprise a light source to illuminate an eye. The main module can comprise an image sensor to receive an image of the eye.

In some embodiments, the interconnect locking structure can comprise a locking ring, and a plurality of interconnect flanges configured to connect the front imaging module and the main module. In some embodiments, the interconnect locking structure has an inner diameter larger than 10 mm and less than 100 mm. In some embodiments, the interconnect locking structure has an inner diameter larger than 20 mm and less than 100 mm. In some embodiments, a first portion of the interconnect locking structure comprises a portion of the front imaging module and a second portion of the interconnect locking structure comprises a portion of the main module. In some embodiments, the interconnect locking structure further comprises a plurality of tracks, wherein the front imaging module is configured to be inserted into the main module through the plurality of mechanical tracks. In some other embodiments, the interconnect locking structure further comprises a plurality of tracks, wherein the main module is configured to be inserted into the front imaging through the plurality of mechanical tracks. In some embodiments, the plurality of interconnect flanges comprise at least 2 pairs of interconnect flanges. In some embodiments, the interconnect locking structure further comprises a plurality of locking pins configured to lock the front imaging module to the main module. In some embodiments, the plurality of locking pins comprise at least 2 pairs of locking pins.

In some embodiments, the interconnect locking structure further comprises a first plurality of electrically conductive power contacts and second plurality of counterpart electrical power contacts. In some embodiments, the plurality of electrically conductive power contacts can comprise a plurality of electrical conductive pins. In some embodiments, the plurality of electrically conductive power contacts are retractable. In some embodiments, the interconnect locking structure can further comprise a first plurality of electrical signal contacts and second plurality of counterpart electrical signal contacts. In some embodiments, the plurality of electrically signal contacts are retractable. The plurality of electrically signal contacts can comprise a plurality of electrical conductive pins.

Various embodiments of the invention comprise a carrying case for an eye imaging apparatus. The carrying case comprises a main portion having an open inner region for storage, a cover configured to cover said inner region of said main portion, a handle configured for carrying said carrying case, at least one of a display monitor, a printer, or a charging station attached to said carrying case. In some embodiments, at least one of a display monitor, a printer, or a charging station is integrated to said carrying case. In some embodiments, said display and printer configured to receive images from said eye imaging apparatus and said charging station configured to charge said eye imaging apparatus.

In some embodiments, the carrying case comprises said display monitor comprising a foldable display monitor configured to be rotatable in a first direction. In some embodiments, said display monitor comprises a foldable display monitor disposed on a multi-axis stand, configured to be rotatable in a first direction and a second direction. The multi-axis stand can comprise a bent hollow tube, a first rotational joint, and a second rotational joint. In some embodiments, a plurality of electrical wires can be disposed inside the hollow tube. In some embodiments, the display monitor has a folded storage position and a working position.

In some embodiments, the cover of the carrying case can be configured to be repeatedly removed and re-attached without employing a tool. In some embodiments, the printer can be attached to the cover. In some embodiments, the printer is attached to the cover and the cover is removable.

In some embodiments, the carrying case can comprise a charging station. The charging station can be attached, or integrated to the carrying case. In some embodiments, the carrying case can further comprise a plurality of retractable electrical contacts, configured to recharge a battery in the eye imaging apparatus. In some embodiments, the carrying case can be configured such that the eye imaging apparatus is capable of being disposed in a first position below the display monitor inside the carrying case to be stored and in a second position in the charging station to be recharged.

In some embodiments, the carrying case is less than 600 mm×400 mm×300 mm. In some embodiments, the carrying case has a volume less than 72,000,000 mm$^3$. In some embodiments, the carrying case can further comprise a computing module integrated in the carrying case, said computing module configured to be in communication with said eye imaging apparatus. In some embodiments, the carrying case can further comprise a communication module integrated in the carrying case, said communication module configured to facilitate communication between said eye imaging apparatus and at least one other device. In some embodiments, the carrying case can further comprise a power entry module and a power on/off switch, said power entry module providing power to one or more of the following, a display, a charging station, a computing module, or a communication module. In some embodiments, the carrying case can comprise at least one region configured to house one or more of the eye imaging apparatus, a wireless keyboard, and a storage container.

Various embodiments of the invention comprise an eye imaging system. The eye imaging system can comprise an eye imaging apparatus and a carrying case for an eye imaging apparatus. The eye imaging apparatus can comprise a light source configured to provide illumination to an eye, imaging optics configured to image said eye, and an optical sensor disposed to receive said image of said eye formed by said imaging optics. The carrying case can comprise a main portion having an open inner region for storage, a cover configured to cover said inner region of said main portion, a handle configured for carrying said carrying case, at least one of a display monitor, printer, or charging station attached to said carrying case.

In some embodiments, the eye imaging system can further comprise a wireless keyboard. In some embodiments, at least one of a display monitor, a printer, or a charging station is integrated to said carrying case in the eye imaging system. In some embodiments, said display and printer configured to receive images from said eye imaging apparatus and said charging station configured to charge said eye imaging apparatus. In some embodiments, said display monitor comprises a foldable display monitor disposed on a multi-axis stand, configured to be rotatable in a first direction and a second direction. The multi-axis stand can comprise a bent hollow tube, a first rotational joint, and a second rotational joint. In some embodiments, the display monitor has a folded storage position and a working position. In some embodiments, the cover of the carrying case can be configured to be repeatedly removed and re-attached without employing a tool. In some embodiments, the printer is attached to the cover and the cover is removable. In some embodiments, the carrying case can comprise a charging station. The charging station can be attached, or integrated to the carrying case. In some embodiments, the carrying case can further comprise a plurality of retractable electrical contacts, configured to recharge a battery in the eye imaging apparatus. In some embodiments, the carrying case can be configured such that the eye imaging apparatus is capable of being disposed in a first position below the display monitor inside the carrying case to be stored and in a second position in the charging station to be recharged. In some embodiments, the carrying case is less than 600 mm×400 mm×300 mm. In some embodiments, the carrying case has a volume less than 72,000,000 mm$^3$. In some embodiments, the carrying case can further comprise a computing module integrated in the carrying case. In some embodiments, the carrying case can further comprise a communication module integrated in the carrying case. In some embodiments, the carrying case can further comprise a power entry module and a power on/off switch, said power entry module providing power to one or more of the following, a display, a charging station, a computing module, or a communication module. In some embodiments, the carrying case can comprise at least one region configured to house one or more of the eye imaging apparatus, a wireless keyboard, and a storage container.

BRIEF DESCRIPTION OF THE DRAWINGS

FIG. 13(A) schematically illustrates a perspective view of an eye imaging apparatus comprising an interconnect locking structure with a locking ring according to various embodiments.

FIG. 13(B) schematically illustrates a side view of an eye imaging apparatus comprising an interconnect locking structure with a locking ring according to various embodiments.

FIG. 14 schematically illustrates an imaging apparatus comprising an interconnect locking structure according to various embodiments.

DETAILED DESCRIPTION

The present invention will be described in detail with reference to the accompanying figures. This invention may be embodied in many different forms and should not be construed as limited to the example embodiments discussed herein.

Figure 1:
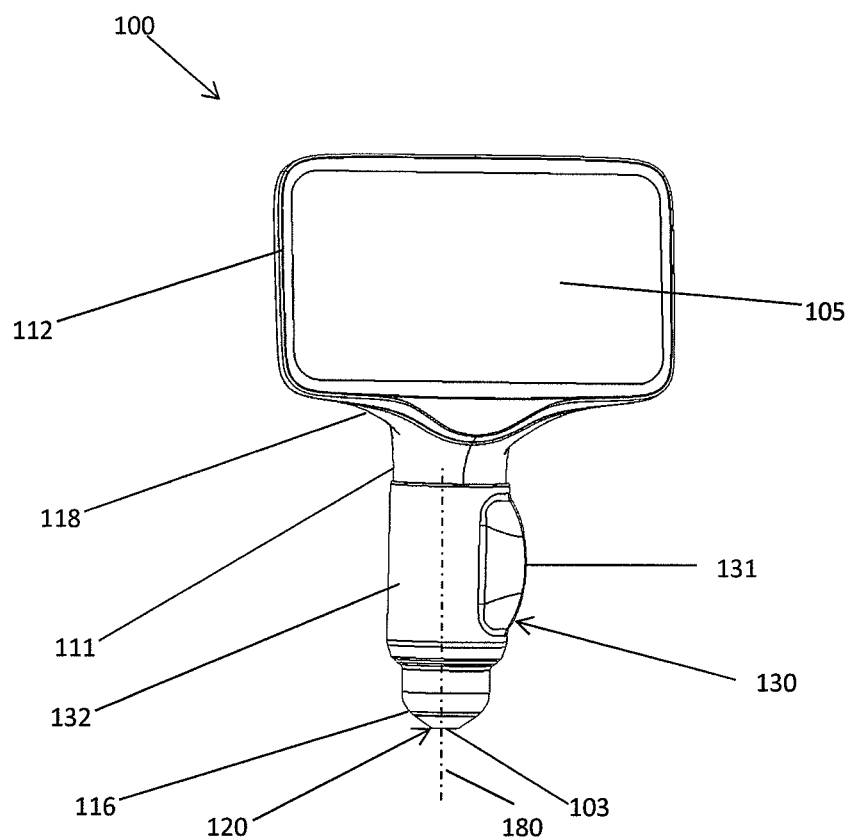
FIG. 1 schematically illustrates an ergonomic eye imaging apparatus comprising a handgrip according to various embodiments of the present invention.

FIG. 1 schematically illustrates an ergonomic eye imaging apparatus 100 comprising a handgrip 130 according to various embodiments of the present invention. The eye imaging apparatus may be compact and in various embodiments has a size less than 250 mm along the longest dimension thereof. For example, in some embodiments the eye imaging apparatus may be between 250 mm and 200 mm, 150 mm, or 100 mm along the longest dimension. In some embodiments, the eye imaging apparatus may weigh less than 1 kg. For example, the eye imaging apparatus may weigh between 1 kg and 0.5 kg, or 0.3 kg, or 0.2 kg in some embodiments. In various embodiments, the eye imaging apparatus is sufficiently light to be conveniently handled, e.g., aligned with the subject or patient's eye, using just one hand. Various embodiments may be easily operated by the operators with little training.

For example, the eye imaging apparatus 100 can comprise a housing comprising a generally cylindrical portion 111 and a generally cuboid portion 112. The cylindrical portion 111 can comprise the imaging optics and illumination light sources, while the cuboid portion can comprise electronic and communication modules. The cylindrical portion 111 can be configured to allow easy grabbing and controlling the imaging apparatus by one hand. The users may precisely adjust the position/tilting angle of the apparatus with one hand, freeing another hand to work on other tasks, for example, opening the eyelids of the patient with the fingers. The cylindrical portion 111 can have a tapered front portion 116, which may be placed closer to an eye of a patient during an examination procedure. The cylindrical portion 111 can have a length between about 50 mm and about 200 mm, and a diameter between about 20 mm and about 80 mm in some embodiments. The front portion 116 of the cylindrical portion 111 can be in a frusto-conical or truncated cone shape with a length between about 10 mm and about 50 mm, and a diameter between about 5 mm and about 20 mm at a very front end 113 in some embodiments.

The cuboid portion 112 can be mounted on top of the cylindrical portion 111 in some embodiments. The cuboid can comprise a touch screen display 105 that is configured to display data and images, as well as control the operation of the ICU. The dimension of the cuboid portion 112 can be between about 50 mm×100 mm and about 130 mm×200 mm in some embodiments. The cuboid portion 112 may be mounted at the top of the cylindrical portion 111, with the touch screen surface tilted at an angle. In various embodiments, the angle may be about 0 degree, 30 degrees, 45 degrees, 60 degrees, 90 degrees or any value between. The cuboid portion 112 may be mounted to the cylindrical portion 111 with the touch screen being perpendicular to the cylindrical portion 111 in some embodiments. The touch screen may also be parallel to the cylindrical portion 111 in some other embodiments. The cuboid portion 112 and the cylindrical portion 111 may be integrally formed, e.g., so as to form a unitary body. The cuboid portion 112 could also be mounted to the cylindrical portion 111, with its length aligned with the axis of the cylindrical portion. In this case, the touch screen display would be configured in a portrait orientation instead of a landscape orientation shown in the FIG. 1. The eye imaging apparatus 100 may comprise only the cylindrical portion 111, or only the cuboid portion 112, in various alternative embodiments. In some embodiments, the housing of the eye imaging apparatus 100 may be in other shapes, not limited to the combination of a cylindrical portion and a cuboid portion.

The eye imaging apparatus 100 can be configured to image both the posterior and the anterior segments of the eye. To image the posterior segment of the eye, an optical window 103 may be carefully placed over the cornea of the eye. The optical window 103 can have a concave surface matching the size of the cornea. In some embodiments, for example, the outer surface of the optical window can have a radius of curvature of between about 6 mm and about 15 mm. An optical index matching gel may be added between the cornea and the optical window to reduce light scattering and optical aberrations. The viscosity of the index matching gel may be at least about 100 centipoise, at least about 200 centipoise, or at least about 300 centipoise in certain embodiments.

The eye imaging apparatus 100 may be compact to improve mobility, maneuverability, and/or portability. For example, in various embodiments, the eye imaging apparatus 100 can have a size less than about 250 mm along the length thereof. For example, in some embodiments, the eye imaging apparatus 100 may be about 250 mm, 200 mm, 150 mm, or 100 mm along the longest dimension. The overall height of the imaging apparatus 100 can be reduced to be less than 200 mm, 175 mm, 150 mm, 125 mm and 100 mm. The diameter of the cylindrical section can be less than 80 mm, 60 mm, 40 mm, and 20 mm.

Various embodiments of the invention comprise an eye imaging apparatus 100 comprising a handgrip 130. The imaging apparatus 100 can comprise a light source and be capable of being powered by an internal battery. All communications can be wireless. Therefore, the imaging apparatus 100 does not have a long communication and/or power cable. In comparison with other eye imaging apparatus with a long cable, because there is no pulling force from the long cable to the imaging apparatus, holding the eye imaging apparatus tightly is easier for the operator. The stress on the operator's hand is also reduced. Thus, precisely aligning the eye imaging apparatus is easier.

In various embodiments, the eye imaging apparatus comprise the handgrip comprising an ergonomic bump. The handgrip 130 can be configured to fit people with different hand sizes and allow the operator to grip the imaging apparatus 100 tightly without extra force. The handgrip 130 can be further configured to enable the operator to tilt the imaging apparatus 100 to different angles and align the touch screen display 105 precisely during an imaging session. The handgrip 130 can also be configured to allow the operator to use either the left hand or the right hand.

In various embodiments, the handgrip 130 can comprise a bump 131 and a hollow ring 132. The bump 131 can be attached to the hollow ring 132 or be built as an integral part of the ring 132. In some embodiments, the hollow ring 132 can be a 360 degree ring that has an inner diameter that fits with the outer diameter of the cylindrical portion 111. For example, the hollow ring 132 can be a tube shaped sheath structure. The handgrip 130 can slide onto the cylindrical portion 111 from the front end 120. The hollow ring 132 comprises elastic material. Accordingly, the inner diameter of the hollow ring 132 is slightly smaller than the outer diameter of the cylindrical portion 111, the hollow ring 132 can be secured on the cylindrical portion 111 of the imaging apparatus 100.

In some embodiments, the handgrip 130 can be removable. The handgrip 130 can have various sizes to fit the sizes of the hands of the operators. In order for the imaging apparatus 100 to be operated comfortably by operators with both large hands, for example, a width of a palm of 82 mm, and small hands, for example, a width of a palm of 60 mm, the diameter of the cylindrical portion 111 is configured to fit the palm size of the operators with small hands. The handgrip 130 can be configured to have different sizes of outer diameters to fit people with different hand sizes. For example, the large size handgrip 130 can be configured to allow comfortable grabbing of the imaging apparatus 100 by the operators with large hands.

In some other embodiments, the handgrip 130 can be fixed to the cylindrical portion 111 of the imaging apparatus 100. The size of the bump 133 can be flexible to fit most of the hands of the operators. In some embodiments, the handgrip 130 comprising the bump 131 can be an integrated portion of the imaging apparatus. The imaging apparatus 100 can comprise a portion in the shape of the handgrip 130 with the bump 131. For example, the bump 131 and the shaft of the cylindrical portion 111 can be a unitary element. The bump 131 can be molded on the housing. In some other embodiments, the bump 131 can be attached to the cylindrical portion 111 by a fastener such as a screw. The size of the bump 133 can be adjustable by a mechanical or an electrical adjustment. For example, the height of the bump 131 can be mechanically adjusted by moving a portion of the bump 131 away from the hollow ring 132.

In various embodiments, the bump 131 can be configured to be rotatable around a central axis 180 of the handgrip 130, which allows the operator to adjust the posture of the hand easily. By doing so, the operator can hold the imaging apparatus 100 closely or at a far distance from the body of the operator. The handgrip 130 can also accommodate the operator with a long or short index finger. The handgrip 130 can be configured to be rotated around the central axis of the handgrip 130 to allow the operator to use either the left or right hand to operate the imaging apparatus 100 as discussed below.

Figures 2A, 2B:
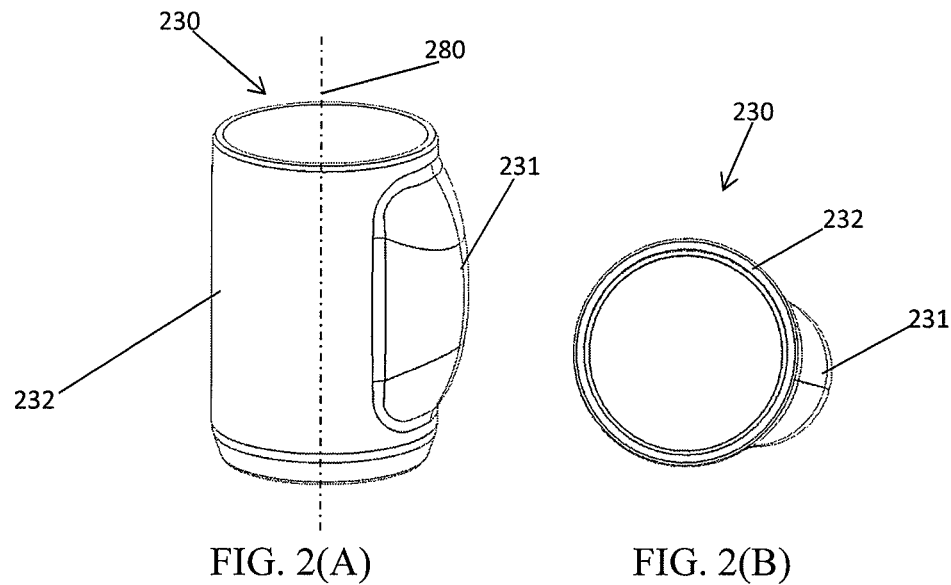
FIG. 2(A) schematically illustrates the side perspective view of the handgrip according to various embodiments.
FIG. 2(B) schematically illustrates the top perspective view of the handgrip according to various embodiments.
Figure 2C:
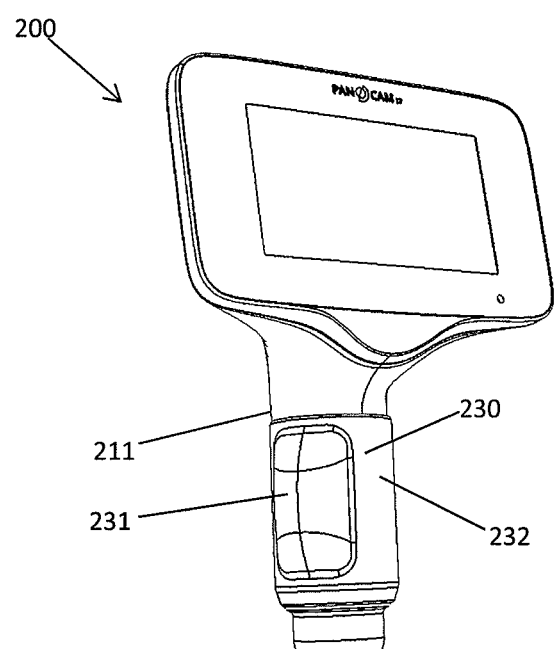
FIG. 2(C) further illustrates the handgrip on the eye imaging apparatus according to various embodiments.

FIG. 2(A) and FIG. 2(B) schematically illustrate the side view and the top view of the handgrip 230 according to various embodiments of the invention. FIG. 2(C) further illustrates the handgrip 230 in the eye imaging apparatus 200 according to various embodiments. Referring to FIG. 2(A), FIG. 2(B) and FIG. 2(C), the handgrip 230 can comprise soft and elastic materials including plastic, rubber, rubber-like materials or combinations thereof. The handgrip 230 can have a length between about 30 mm and about 200 mm, and a diameter between about 20 mm and about 80 mm in various embodiments. The inner diameter of the hollow ring 232 of the handgrip 230 can match the outer diameter of the cylindrical portion 311 of the imaging apparatus 200, or be slightly smaller than the outer diameter of the cylindrical portion 311. The thickness of the handgrip 230 can be between 1.0 mm to 20.0 mm.

As shown in FIG. 2(A) and FIG. 2(B) and discussed above, the handgrip 230 can comprise an ergonomic bump 231. The bump 231 can be positioned at a side of the hollow ring 232. The bump 231 can be shaped to fit comfortably with a palm of an operator, allowing the operator to hold the imaging apparatus 200 in the palm tightly by clasping with four fingers, including a middle finger, a ring finger, a pinky finger and a thumb. The bump 231 can have a convex shape to fill a space between the imaging apparatus 200 and a palm of an operator. The bump 231 can be configured to have a profile closely match a contour of a palm of the operator when the operator is holding the imaging apparatus 200. The bump 231 can comprise an extra volume to fill the space between the imaging apparatus 200 and the palm of the operator. The bump 231 allows use of less force in order to secure the imaging apparatus 200 by one hand. In addition, the bump 231 can also be configured such that a thumb can clasp around the cylindrical portion 311 tightly. The profile of the bump 231 can be further configured to match a contour of a thumb. In various embodiments, the eye imaging apparatus can comprise a handgrip having a contour that provide ergonomic benefits. The handgrip 230 can be disposed on a portion of the imaging apparatus 200 that houses at least a portion of the imaging optics, light source, image sensor, or combinations thereof. For example, the handgrip 230 can be disposed on the cylindrical portion 211 of the imaging apparatus 200, wherein the cylindrical portion 211 houses the imaging optics, light source, and/or image sensor of the eye imaging apparatus 200.

In some embodiments, the contact surface of the bump 231 is configured to fit the palm of the operator comfortably and provide some texture. In some embodiments, the contact surface of the bump 231 can be configured to fit the palm of the operator comfortably and provide a level of traction, or friction. This texture, traction or friction of the imaging apparatus 200 can reduce the risk of the imaging apparatus 200 slipping in the user's hand. The maximum height of the bump 231 can be between 5 mm to 60 mm. When the space between the imaging apparatus 200 and the palm of the operator is filled by the handgrip 230, the imaging apparatus 200 is secured comfortably. The operator can use three fingers including the middle finger, the ring finger and the pinky finger to clamp down on the cylindrical portion 211 with the thumb pressing on the imaging apparatus 200. The use of the handgrip 230, especially the bump 231 on the handgrip 230, enables true one-hand operation of the imaging apparatus 200 as well as freeing an index finger of the operator.

The handgrip 230 can be configured to fit different sizes of the hands of the operators. The bump 231 and the hollow ring 232 can be replaced easily. Several rings 232 can be provided with different bump sizes to fit operators who have large or small hands. The hollow ring 232 may be rotated along the cylindrical portion 211 of the imaging apparatus 200, thus allowing a comfortable fitting with the palm of the operator's hand. The rubber grip ring 232 may fit with both left-handed and right-handed operators. The bump 231 can allow the use of less force by hand in order to secure the body of the imaging apparatus 200 in one hand compared to configurations without the bump. The bump 231 can be rotatable around a central axis 280 of the handgrip 230, which allows the operator to adjust the posture of the holding easily. By doing so, the operators can hold the imaging apparatus 200 in different positions, for example, close to the bodies of the operators or away from the bodies of the operators.

As discussed above, the position of the bump 231 can be configured to be adjustable to accommodate the left-handed or right-handed operators. The bump 231 can be adjusted to the left or right side of the cylindrical portion 211 of the imaging apparatus 200 to accommodate the left-handed or right-handed operators. In some embodiments, the position of the bump 231 can be adjusted by rotating the handgrip 230 around the cylindrical portion 211 of the imaging apparatus 200. In some other embodiments, the position of the bump 231 can be adjusted by removing the handgrip 230 from the imaging apparatus 200, and reattached the handgrip 230 to the imaging apparatus 200 in a different orientation.

The handgrip 230 and the bump 231 can comprise many different shapes and many different structures. For example, the hollow ring 232 can also comprise various shapes other than a completed ring, e.g., such as a partial annulus. The hollow ring 232 thus may have the shape of a "C" or "U" or arc ranging from about 30 degrees, 60 degrees, 180 degrees, 270 degrees to less than 360 degrees. The bump 231 may have a top surface shaped to fit the contour of the palm of the operator and a side surface shaped to fit the contour of the thumb, middle finger, ring finger and the pinky finger. The handgrip 230 can have a second bump in addition to the first bump. The second bump can be positioned along the same vertical direction with and above the first bump, when the patient's eye is below the cylindrical portion 211 of the imaging apparatus 200. The second bump can have a profile configured, for example, to match the contour of the thumb of the operator.

Figure 3A:
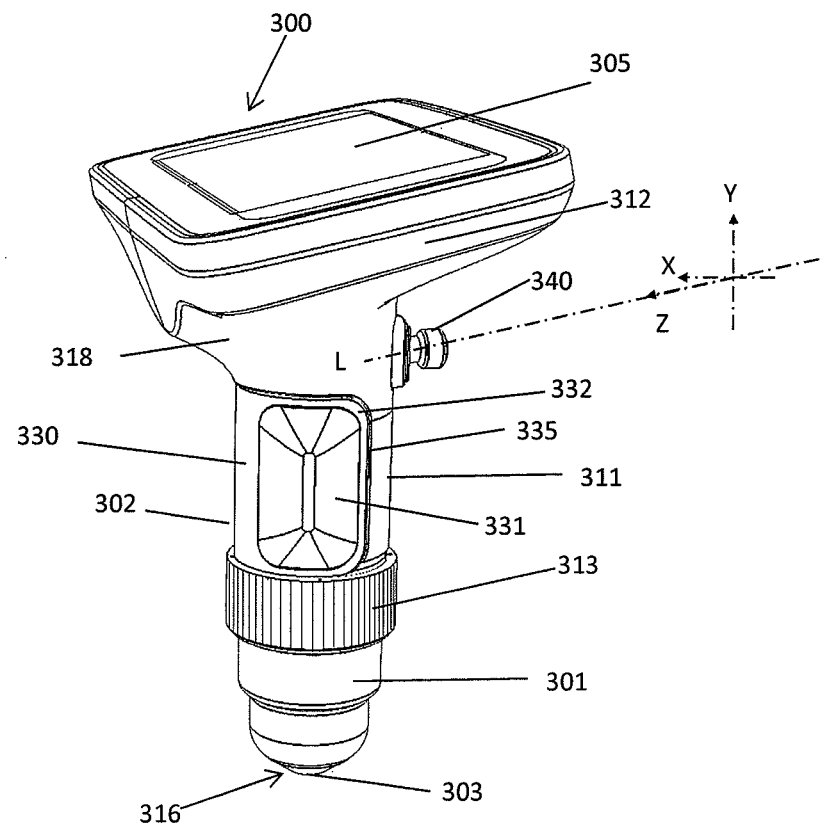
FIG. 3(A) schematically illustrates an alternative embodiment of the handgrip comprising a partial ring structure as well as a multi-functional control button on the imaging apparatus.

FIG. 3(A) schematically illustrates some alternative embodiments of handgrip 330 of the imaging apparatus 300. As discussed above, in some embodiments, the handgrip 330 can comprise a partial ring structure 332. The partial ring structure 332 can be 30 degree, 60 degree, 90 degree, 180 degree, 270 degree, or 359 degree, or any value between. The wrapping structure can be configured to be snapped-on to the cylindrical portion 311. The imaging apparatus 300 can further comprise an interlock borderline 335. The interlock borderline 335 can be a dovetail structure underneath the handgrip 330 to tightly lock the handgrip 330 with the cylindrical portion 311 of the imaging apparatus 300. In various embodiments, the interlock borderline 335 can be positioned near the edge of the handgrip 330. In some embodiments, the handgrip 330 cannot be rotated around the cylindrical portion 311. However, the handgrip 330 can be removed and then flipped over to be snapped-on or clicked-on to the cylindrical portion 311, which effectively provides accommodation for the left-hand and right-hand operators. In some embodiments, the handgrip 330 can be removed from the imaging apparatus 300 and reattached to the imaging apparatus in a different direction. Advantageously, therefore, in various embodiments a user can conveniently remove and reattach the handgrip 330 multiple times without using tools.

As discussed above, the handgrip 330 can comprise soft and elastic materials including plastic, rubber and rubber-like materials or combinations thereof. The handgrip 330 can have a length between about 20 mm and about 150 mm, and a diameter between about 20 mm and about 80 mm in some embodiments. The inner diameter of the handgrip 330 can match the outer diameter of the cylindrical portion 311 of the imaging apparatus 300. The thickness of the handgrip 330 can be between 0.1 mm to 30 mm. The handgrip 330 can comprise a bump 331. The bump 331 can be shaped to fit comfortable in the palm of the operator. The bump 331 can comprise extra volume to fill the extra space between the imaging apparatus 300 and the palm of the operator. The profile of the bump 331 can be configured to match a contour of a palm of the operator when the palm is in the holding position. In addition, the bump 331 can be configured such that the thumb can clasp around the cylindrical portion 311. For example, the bump 331 is configured to have a profile in a shape of a portion of ellipsoid, or parabolic in shape at the cross-section, or any other convex shape. In some embodiments, the handgrip 330 comprises a first portion with a circular cross section, and a second portion with an elliptical, parabolic shape, or other convex shape cross-section attached to the first portion. In some other embodiments, the handgrip 330 can comprise a cross-section, partially in circular shape, and partially in elliptical, parabolic shape or other convex shape. In some alternative embodiments, the handgrip may have a shape that is non-symmetrical or asymmetrical. For example, the handgrip 330 can have a non-symmetric convex profile along a vertical and/or horizontal direction, such that the non-symmetric convex shape fits comfortably with the palm of the operator. In some embodiments, the handgrip bump has a cross-section that is non-symmetrical with respect to an axis along the length of the cylindrical portion 311 that is parallel to the Y axis shown in FIG. 3(A) and/or with respect to an axis along the width of the cylindrical portion 311 that is parallel to the X axis shown in FIG. 3(A). In some embodiments, the handgrip bump may have a cross-section that is non-symmetrical with respect to an axis along the length of the bump and/or with respect to an axis along the width of the bump.

The maximum height of the bump 331 can be between 5 mm to 40 mm. The direction of the height of the bump 331 is normal to the surface of the shaft of the imaging apparatus 300. The bump 331 can have a length between about 20 mm and about 150 mm. The bump 331 can have a width between about 5 mm to 40 mm. The length of the bump 331 is along the surface of the shaft, in a direction extending from the front end to the back end of the imaging apparatus 300. The width of the bump 331 is along the surface of the shaft, from the right side to the left side. The bump 331 can have a length between about 20 mm and about 150 mm. The bump 331 can have a width between about 5 mm to 40 mm. In some embodiments, the bump 331 can have a length larger than the width. In some other embodiments, the bump 331 can have a length smaller than the width. In some alternative embodiments, the bump 331 can have a length equal to the width. When the extra space is filled by using the handgrip 330, the imaging apparatus 300 is secured comfortably.

The contact surface of the bump 331 can be configured to fit the palm of the operator comfortably and with a high level of friction or traction, which can prevent the imaging apparatus 300 from slipping. The use of the handgrip 330, especially the bump 331 on the handgrip 330, enables true one-hand operation of the imaging apparatus 300 as well as freeing an index finger of the operator.

Figure 3B:
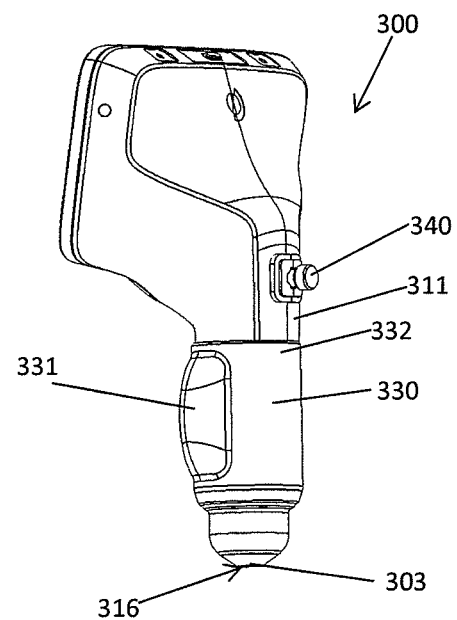
FIG. 3(B) schematically illustrates an eye imaging apparatus comprising the multi-functional button according to various embodiments.

The eye imaging apparatus 300 may be built as one piece or two separate pieces as schematically illustrated in FIG. 3(A) and FIG. 3(B). In some embodiments as illustrated in FIG. 3(A), the eye imaging apparatus 300 can comprise a housing which comprises two portions, a front imaging module portion 301 and a main module portion 302 with a touch screen display 305. The front imaging module 101 may be removed or replaced with other functioning modules which may contain different optics. For example, front imaging modules with higher magnification, front imaging modules designed for premature babies, front imaging modules designed for adult, front imaging modules designed for fluorescein angiography imaging, front imaging modules for NIR imaging and front imaging modules for anterior segment imaging can be used in different circumstances. Accordingly, in designs where the front imaging module is replaceable or removable, the potential use or applications of the imaging apparatus 300 may be significantly expanded. An optical window 303 is exposed on the outside of the housing of the imaging apparatus 300 enabling light to enter into and exit out of the housing. In various embodiments, the eye can be placed proximal to or up against the optical window 303 to obtained images of the eye. As discussed above, this window 303 can be concave to receive the cornea. The imaging apparatus can further comprise a locking ring 313 which will be discussed below.

In some other embodiments as illustrated in FIG. 3(B), the imaging apparatus 300 can have a single piece housing that is not designed to be separated into pieces by the user unlike the housing shown in FIG. 3(A). The optical window 303, possibly concave, can be exposed on the outside of the housing of the imaging apparatus 300 enabling light to enter into and exit out of the housing. The handgrip 330 can comprise the ring or the partial ring 332 comprising the ergonomic bump 331. The handgrip 330, especially the bump 331 on the handgrip 330, enables one-hand operation of the imaging apparatus 300 as well as freeing an index finger of the operator.

Figure 3C:
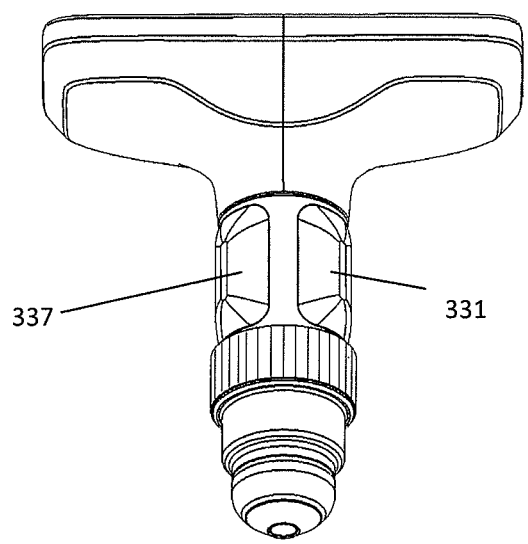
FIG. 3(C) schematically illustrates some alternative embodiments of the handgrip of the imaging apparatus.

FIG. 3(C) schematically illustrates some alternative embodiments of handgrip 330 of the imaging apparatus 300. In some embodiments, the handgrip 330 can comprise a second bump 337, which is positioned in on another side of handgrip 330, in addition to the first bump 331. The second bump 337 is positioned at a different vertical direction along the length of the cylindrical portion than the first bump 331, but at the same horizontal plane normal to the length of the cylindrical portion as the first bump 331. The first bump 331 is configured to be comfortable for most of right-hand operators, and the second bump 337 is configured to be comfortable for most of left-hand operators. Such a configuration can eliminate the adjustment step for the imaging sessions between the right-hand and left-hand operators. The second bump 337 has little effect for the right-hand operators, while the first bump 331 has little effect for the left-hand operators. As described above, either or both the first and second bumps can be asymmetric. In some embodiments where both bumps are asymmetric, the asymmetry of the second bump can be opposite to or reversed as compared to the first bump. For example the first bump can be a mirror image of the second bump. The first and second bumps, however, need not be mirror images but may nevertheless be oppositely directed, oriented, or shaped. Such orientations may facilitate fitting with right and left hands respectively.

In order for one operator to tightly grab the imaging apparatus 300 and control the imaging session by one hand, a joystick style multi-functional control button 340 can be used to allow one-hand operation. As shown in FIG. 3(A) and FIG. 3(B), the imaging apparatus 300 can further comprise a multi-functional control button 340, which can comprise a multi-functional joystick positioned on the cylindrical portion 311 to allow the operator to control the imaging apparatus 300 with a single hand and manipulate the multi-functional control button 340 with the index finger.

Figure 3D:
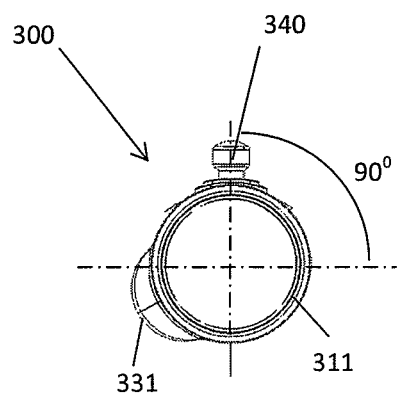
FIG. 3(D) schematically illustrates an orientation of the multi-functional button and the bump of the eye imaging apparatus according to various embodiments.

FIG. 3(D) schematically illustrates an orientation of the multi-functional button 340 and the bump 331 of the eye imaging apparatus 300 according to various embodiments. The multi-functional control button 340 is a multi-directional, multi-functional joystick type of button, configured to perform focus adjusting, brightness adjusting, and image capturing functions. The handgrip 330 can be configured to allow the operator to comfortably reach and control the joystick type multi-functional control button 340 with the index finger. The multi-functional control button 340 can be positioned in a central location on the cylindrical portion 311 symmetrical to the left or right side, which allows for both the right-handed operation and left-handed operation. The multi-functional control button 340 can be configured to have left right symmetry to accommodate left hand and right hand operation. For example, looking from the top, the multi-functional control button 340 can be positioned at 90 degrees azimuthally with respect to the central axis through the cylindrical portion 311. The bump 331 can additionally be rotatable from 270 degrees to 360 degrees for the right-handed operators and from 180 degrees to 270 degrees for the left-handed operators as shown in FIG. 3(D).

In an imaging session using the eye imaging apparatus 300, the operator may use the palm of the left hand to hold a patient's forehead to prevent the movement of the head, and use an index finger and a thumb of the left hand to form a buffer over the eye cup between the eye of the patient and the front end 316 of the imaging apparatus 300. Such posture can not only support a portion of the weight of the imaging apparatus 300, but also prevent accidental impact of the patient's eye from the imaging apparatus 300 when the sudden motion of the patient's head or the imaging apparatus 300 occurs. The operator can then use the right hand to hold and operate the imaging apparatus 300. In order for the operator to tightly hold the imaging apparatus 300 and control the multi-functional control button 340 at the same time, the imaging apparatus 300 can be configured to be held by the three fingers of the right hand including the middle finger, the ring finger and the pinky finger. The operator can also use the thumb of the right hand to help to secure the imaging apparatus 300 by grabbing around the cylindrical portion 311 of the imaging apparatus 300 from another side. The handgrip 340 is configured to enable the operator to hold and secure the imaging apparatus 300 by using only four of five fingers of one hand, thus freeing an index finger to manipulate the joystick type multi-functional control button 340.

The configuration of the handgrip 330 with the bump 331 can enable the operation of the imaging apparatus 300 by the free index finger to control the multi-functional control button 340. The handgrip 330 can also accommodate operators with long or short index fingers to ensure that the operators can always place their index fingers on the top of the multi-functional control button 340 comfortably. Operators with hands of average size can curve the index fingers a little bit in order to operate the multi-functional control button 340 with the distal phalanx. Operators with small hands can fully extend their index fingers in order to reach the multi-functional control button 340 with the distal phalanx.

Figure 3E:
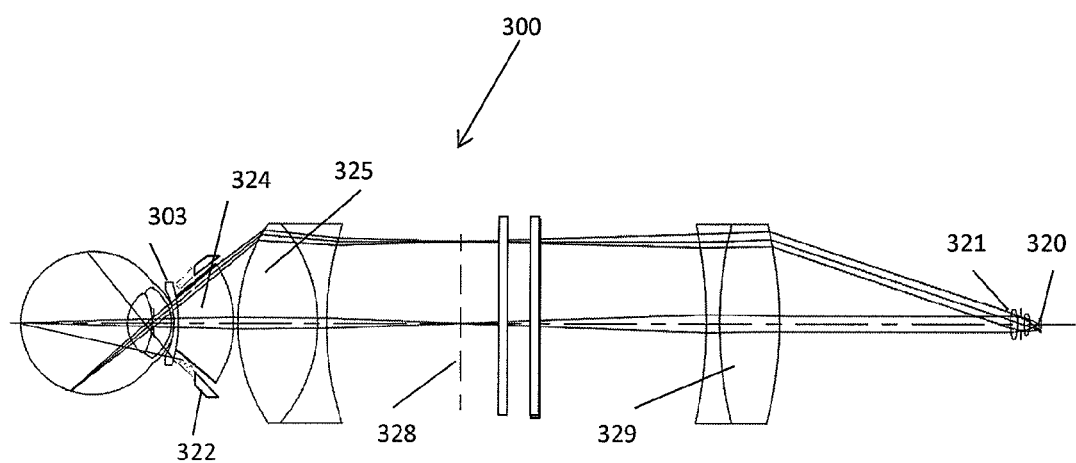
FIG. 3(E) schematically illustrates an optical layout of the eye imaging apparatus according to various embodiments.

FIG. 3(E) illustrates the schematics of the optical layout of the eye imaging apparatus 300 according to various embodiments of the invention. The eye imaging apparatus 300 can be configured to image both the posterior and the anterior segments of the eye. To image the posterior segment of the eye, an optical window 303 may be carefully placed over the cornea of the eye. The illumination light can be projected from the optical window 303. A light source with a light conditioning element 322 may be used to project the light through the designated areas on the cornea and the crystalline lens of the eye, and eventually onto the posterior segment of the eye. An imaging lens 324 behind the optical window 303 may be used to form an image of the posterior segment, which includes the space from the retina and the posterior vitreous chamber of the eye. A first group of relay lenses 325 may be used to relay the image of the posterior segment to a secondary image plane 328. A second group of relay lenses 329 may be added to relay the image from the secondary image plane 328 onto the image sensor 320. The image sensor 320 may be any suitable type of imaging sensor, e.g., a CCD or CMOS sensors. Other type of image sensors may also be used. The eye imaging apparatus 300 may comprise at least one focusing lens 321 positioned in front of the image sensor 320. The focusing lens or lenses 321 may be configured to adjust a focal length or a magnification of the eye imaging apparatus 300. In various embodiments, one or more of the focusing lenses 321 can be configured to be moved or adjusted. For example, one or more of the focusing lenses 321 can be translated longitudinally along an optical axis of the optical imaging system with respect to one or more of the other of the focusing lenses in the lens group 321. Displacing the focusing lenses 321 relative to one another may change the effective optical focal length of the set of focusing lenses 321, which can change the magnification and can result in an optical zoom for the images acquired. Actuators such as voice coils, stepper motors or other types of actuators or combinations thereof may be used to longitudinally translate one or more, or all, of the focusing lenses to change the effective focal length(s) and/or provide zoom. During an eye imaging procedure, the focusing lens or lenses 321 may be controlled manually or automatically. In the fully automatic mode, the eye imaging apparatus 300 may automatically look for features in the images and try to adjust the actuator of the focusing lens or lenses 321 to achieve the best focus. In the manual mode, the users may select the area of focus over the live images. The eye imaging apparatus 300 may adjust the focusing lens or lenses 321 to achieve the best focus in that area and then provide a visual or audible indication when the area is in focus. The image brightness or exposure may also be controlled through automatic or manual mode. In the automatic exposure mode, the operators may allow the eye imaging apparatus 300 to adjust the brightness of the images automatically based on preset imaging criteria. Alternatively, the operators may fine tune the exposure by gauging the proper exposure at a selected area in the image, which is often also the area for fine focus adjustment. The overall brightness of the image may be adjusted or set by the operators according to their preference. The brightness of the image may be controlled by the sensitivity of the image sensor 320 or luminance of the light source 322. In some embodiments, the sensitivity of the image sensor 320 can be set to a fixed level when the quality of the images or the noise level of the image is a critical measure. The luminance of the light source 322 can be adjusted to achieve the desired brightness based on the darkness of the retinal pigmentation layer. A maximum level of allowable luminance may be set in order to prevent the illuminance from exceeding the level allowed by regulations due to the concern of phototoxicity to the eye. During the imaging session, the operator may spend a significant amount of time adjusting the image brightness, focus, and field of view while viewing the live images on the screen. The operator may capture few pictures in a short time afterwards. In some embodiments, to reduce the amount of light to which the patient's eye is exposed, the sensitivity of the image sensor during the adjustment process may be configured to increase by a suitable amount, e.g., by 2 or 4 times higher than the desired level of sensitivity during the imaging session when the images are captured. The increased sensitivity may accordingly result in a reduction in the level of illumination light by 2 or 4 times, although such increase in sensor sensitivity may cause a higher noise level and poor image quality for the live images. When the operator captures still pictures during the imaging session, the sensitivity of the image sensor may be configured to momentarily decrease to the desired level to provide acceptable image quality. At the same time, the amount of illumination light can be configured to increase by the same ratio momentarily, which may result in the same exposure and brightness for the still images with higher image quality and a lower noise level. The increase of the sensor's light sensitivity during the adjustment process may be 2 times, 3 times, 5 times, 8 times and any level between, higher than the desired sensitivity level during the imaging session. In some alternative embodiments, the level of the luminance from the light source 322 may be fixed or selected by the operators when a specific level of light exposure is desired. The sensitivity of the image sensor 320 may accordingly be adjusted automatically.

Now, referring to FIG. 3(A) to FIG. 3(E), the multi-functional control button 340 can comprises a multi-directional button comprising one or more electrical switches configured to control parameters of the eye imaging apparatus 300. The control parameters of the eye imaging apparatus 300 can comprise the focus, zoom, magnification, intensity, brightness, imaging capturing trigger and other parameters. In some embodiments, the multi-functional control button is configured to control a least two of the light source 322, illumination optics, the imaging optics, the image sensor 320, and imaging processing. The illumination optics can comprise a shutter, a light conditioning element, a plurality of light emitting elements and other illumination elements. In some other embodiments, the multi-functional button can be configured to control the light source 322, the actuator of a focusing lens or lenses 321 and the image sensor 320. In some embodiments, for example, the multi-functional control button 340 can be disposed on the cylindrical portion 311 of the housing of the eye imaging apparatus 300, thus allowing easy operation for the operator with only one hand. The eye imaging apparatus 300 may be held by the operator using four fingers, while leaving the index finger (or other finger) free to operate the multi-functional control button 340 in some embodiments. The introduction of the multi-functional control button 340 can enable the operation of the imaging apparatus 300 with only one hand. The multi-functional control button 340 can be configured to be pushed back-and-forth in two orthogonal directions X and Y in a plane perpendicular to a radial line L of the cylindrical portion 311 and click in a direction Z along the radial line L. The multi-functional control button 340 can comprise electrical switches to control the light source 322, the actuator of the focusing lens or lenses 321 and/or the image sensor 320. Therefore the multi-functional control button 340 can allow the operator to control the focus, the light intensity and/or the image capturing process by using just one finger. For example, in some embodiments, the intensity level of the light source 322 may be adjusted by pushing the multi-functional control button 340 to the left and/or right, and the actuator of the focusing lens or lenses 321 may be adjusted by pushing the multi-functional control button 340 up and/or down. In other embodiments, the intensity level of the light source 322 may be adjusted by pushing the multi-functional control button 340 up and/or down, and the actuator of the focusing lens or lenses 321 may be adjusted by pushing the multi-functional control button 340 left and/or right. In some embodiments, the multi-functional control button 340 may also be used as a trigger for the image sensor 320 by pushing the multi-functional control button 340 inwardly. Other variations of using the multi-functional control button 340 to control the eye imaging apparatus may also be suitable.

In some embodiments the control button 340 need not be multi-functional. Instead the control button 340 can be used to provide control of one feature such as one of the feature discussed above. In some embodiments, for example, the control button 340 is a trigger that when pressed or pulled inward and/or downward will cause the sensor to capture an image. The single function button can be configured for a different purpose in alternative embodiments.

In other embodiments, the control button 340 can be configured to move sideways (e.g., left and/or right), to provide control of a parameter of the imaging apparatus. In yet other embodiments, the control button 340 can be configured to move up and/or down, to provide control of a parameter of the imaging apparatus.

In various embodiments the control button 340 is configured to be actuated by the index finger. For example, the control button 340 may be disposed with respect to the bump to that fits with the palm of the hand to position the control button 340 proximal to the index finger for convenient actuation.

In certain embodiments, the control button 340 permits movement sideways, up and down or inward and receives input based on such movements. In certain embodiments, the control button 340 comprises a multi-function control button that permits movement in two of these directions such as sideways and up and down, or sideways and inward, or up and down an inwards to control multiple parameters. As described above, the multi-control button may also permit movement in all three of these directions and receive input to control the imaging apparatus based on such movements.

As discussed above, in various embodiments, the housing of the imaging apparatus 300 can comprise the cylindrical portion 311, the cuboid portion 312 and a transition portion 318 between the cylindrical portion 311 and the cuboid portion 312, as illustrated in FIG. 3(A). In order to enable the operators to perform imaging session comfortably and conveniently, especially for a large volume of patients, the profile of the transition portion 318 can have a shape that matches the contour of the top side of the hand of the operator. The shape of the transition portion 318 can be configured to enable most of the weight of the imaging apparatus being supported by a top side of the hand, thus allowing the fingers to operate controls easily.

Figure 4:
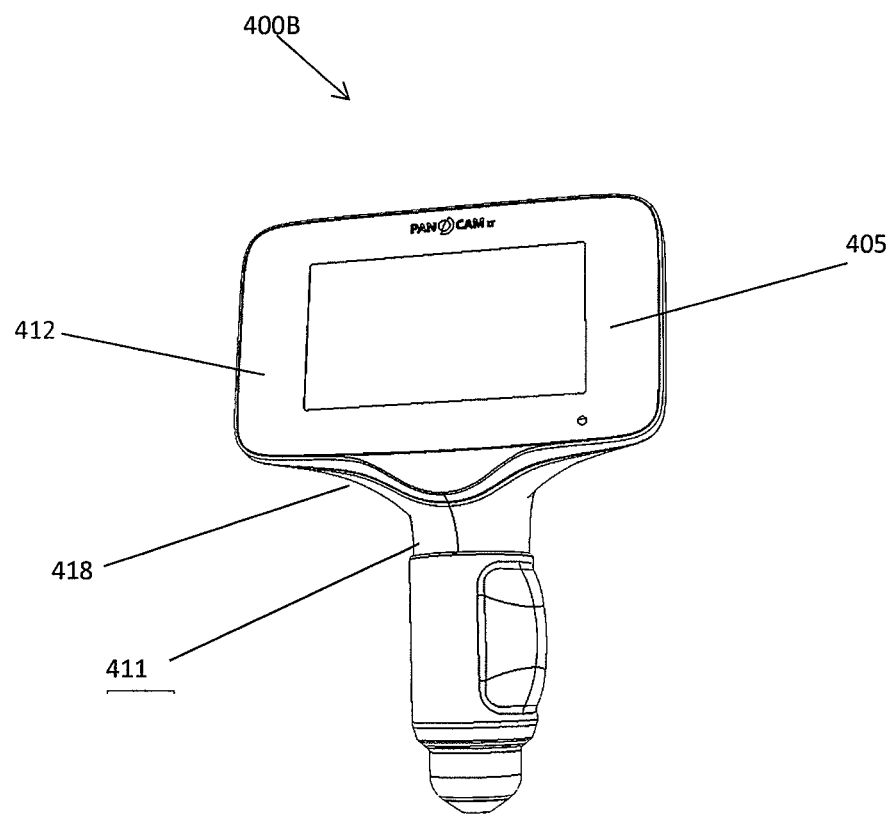
FIG. 4 schematically illustrates the transition portion of the eye imaging apparatus according to various embodiments.

FIG. 4 schematically illustrates the structure of the transition portion 418 of the imaging apparatus 400 with a touch screen display 405 positioned parallel to the cylindrical portion 411 in some other embodiments. The shape of the transition portion 418 is configured to support most of the weight of the imaging apparatus 400 by the top side of the hand of the operator. When the top side of the hand supports most of the weight of the imaging apparatus 400B, three fingers (the middle finger, ring finger and pinky finger) can hold and align the imaging apparatus 400B, including tilting the apparatus 400 in different directions, and the index finger can operate the multi-functional control button 440 to adjust the brightness, focus and capture the images conveniently.

Figure 5:
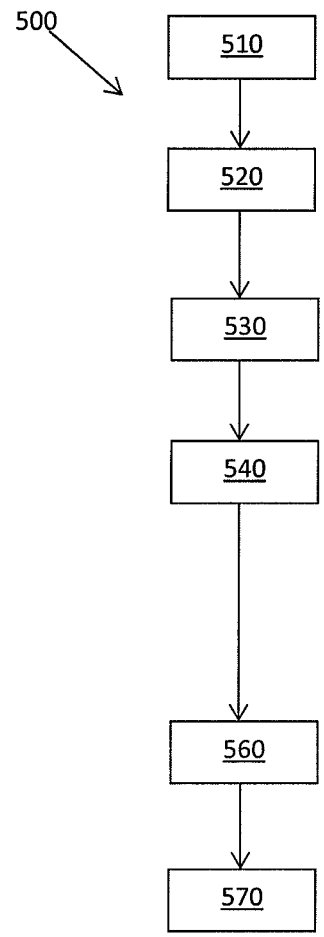
FIG. 5 schematically illustrates a block diagram of a method of operating the eye imaging apparatus according to various embodiments.

FIG. 5 schematically illustrates a block diagram of a method to operate the eye imaging apparatus 500 according to various embodiments of the invention. The method can comprise selecting a size of a handgrip that matches a size of a hand of an operator 510, sliding the handgrip onto a cylindrical portion of the eye imaging apparatus 520, rotating the handgrip until it is at the location for right-handed operation or left handed operation 530 that provides comfortable placement of the index finger on the multi-functional button. The method can comprise using the three fingers including the middle finger, the ring finger and the pinky finger to hold the handgrip, and using a thumb to secure the imaging apparatus 540. The method can comprise aligning the position of the imaging apparatus by the thumb and the three fingers including the middle finger, the ring finger and the pinky finger 560. The method can further comprise using the index finger to operate the multi-functional control button to adjust the brightness, focus and capture the images 570.

Figure 6:
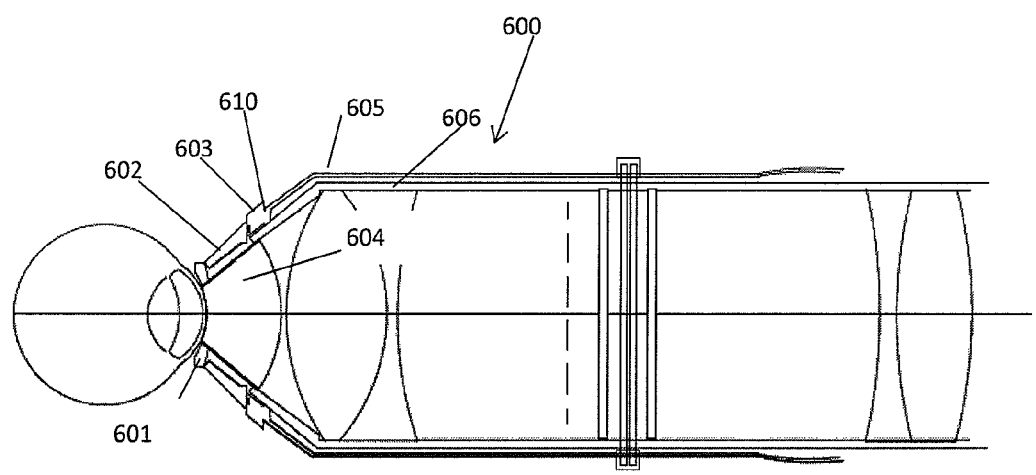
FIG. 6 schematically illustrates the eye imaging apparatus comprising a light source and a heat sink according to various embodiments.

FIG. 6 schematically illustrates various embodiments of the eye imaging apparatus 600 comprising a light source 603 and a heat sink 610. The light source 603 of the eye imaging apparatus 600 can emit light in the visible spectrum, IR spectrum, near IR spectrum and/or UV spectrum. In some embodiments, the light source 603 can comprise a plurality of light emitting elements. The light emitting elements can include solid state light emitters such as light emitting diodes and/or any other elements that are capable of emitting light. The light emitting elements can be compact, highly efficient and driven by low voltage. The light source 603 and the heat sink 610 can be placed directly against the light conditioning element 602. The heat sink 610 can be used to disperse the heat generated by the light source 603. The light from the light sources 603 is directed into the posterior segment of the eye through the light conditioning element 602 and optical window 601. The light source 603, together with the heat sink(s) 610, can be disposed on an outer surface of an inner shell 606 which houses the optical imaging system including at least part of the imaging lens 604. This shell can comprise, for example, a tube or ring. The light source 603 can be powered electrically through the electric wires 605 laying along the outer surface of the inner shell 606.

Figure 7:
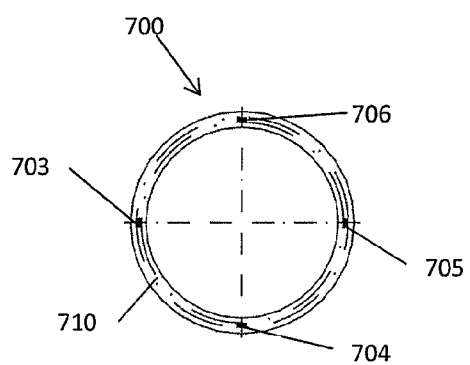
FIG. 7 schematically illustrates an eye imaging apparatus comprising light emitting elements and the heat sink according to various embodiments.

FIG. 7 schematically illustrates an eye imaging apparatus 700 comprising a plurality of light emitting elements 703 and a heat sink 710 according to various embodiments of the invention. In some embodiments, the light emitting elements 703 can be mounted onto the heat sink 710 comprising a ring to increase a mass of the heat sink, thus increasing heat dissipation capability. The light emitting elements can be activated sequentially or simultaneously or be activated in any desired order. FIG. 7 shows an embodiment with 4 light emitting elements 703, 704, 705, and 706 at 0°, 90°, 180°, and 270° azimuthal positions on an annular heat sink 710.

Figure 8:
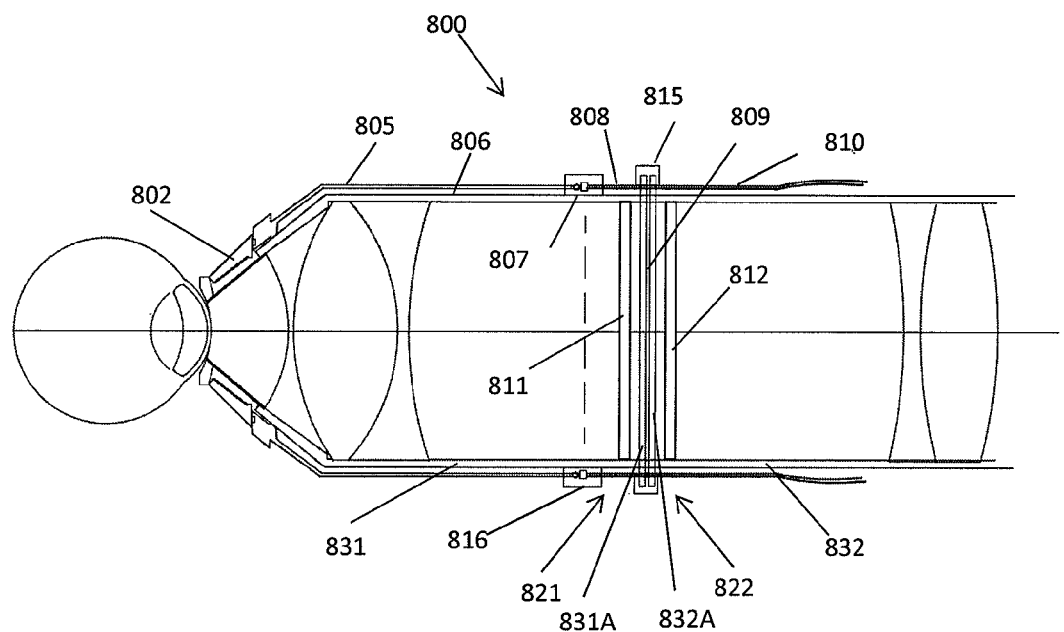
FIG. 8 further schematically illustrates an embodiment of the heat sink in the eye imaging apparatus.

FIG. 8 further schematically illustrates various embodiments of the heat sink 816 in the eye imaging apparatus 800. In some embodiments, one or more optical fibers 805 are used to guide the light from the light source 807 to the light conditioning element 802. The light source 807 can be mounted to a large ceramic/metal heat sink base 816, in order to increase the heat dissipation capability. The heat sink 816 can comprise a ring shape structure comprising ceramic, metal, or other thermal conductive materials. The heat sink 816 can also be in contact with the inner shell 806 in order to dissipate the heat.

In various embodiments, the eye imaging apparatus 800 can comprise two separate modules such as a front imaging module 821 and a main module 822, which are separated at an interface 809. The inner shell 806 which houses the optical imaging system can comprise a forward lens shell 831, which houses the lenses in the front imaging module 821, and a rearward lens shell 832, which houses the lens in the main module 822. One or more electric connectors 815 can be used to interconnect the wires 808 in or on the front module 821 and the wires 810 in or on the main module 822. To prevent dust from entering the housings and depositing on the optics, two optical windows 811 and 812 can be used to seal off the housings. If a single piece construction is used, then the electric interconnection 815 and the optical windows 811, 812 can be excluded, with the inner shell comprising front and rear portions that need not be separable. If the heat sink 816 is positioned next to the interconnection surface 809, the inner shell 806 can further comprise a pair of matching heat conducting surfaces 831A and 832A comprising, for example, copper or other materials having good thermal conductivity along the interconnection surface 809, as part of an extension of the forward lens shell 831 and the rearward lens shell 832 in the front imaging module 821 and the main modules 822. When the removable front imaging module 821 is attached to the main module 822, the two heat conducting surfaces can contact each other, thus permitting transfer of the heat from the lighting source 807 to the larger mass in the main module 822. Such a design may reduce the temperature of the imaging apparatus housing 800, especially the housing of the removable front imaging module 821, which the operator may employ to hold the imaging apparatus 800 in various embodiments.

Figure 9:
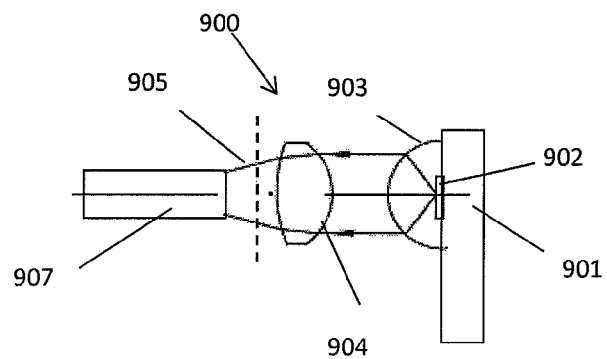
FIG. 9 schematically illustrates an embodiment of an eye imaging apparatus wherein a light source comprising, for example, a light emitting element, is mounted onto a heat sink base.

FIG. 9 schematically illustrates various embodiments when a light source 902, for example, a light emitting element, is mounted onto a heat sink base 901 of an eye imaging apparatus 900. In some embodiments, the light from the light source 902 is initially collimated by a dome lens 903. The collimated light is coupled to the fiber optical bundle 907 through a coupling lens 904. The light source 902 has a base 901 that is mounted onto a heat sink base. The coupling optical lens 904 can be pre-aligned with the light emitting element 902.

Figure 10:
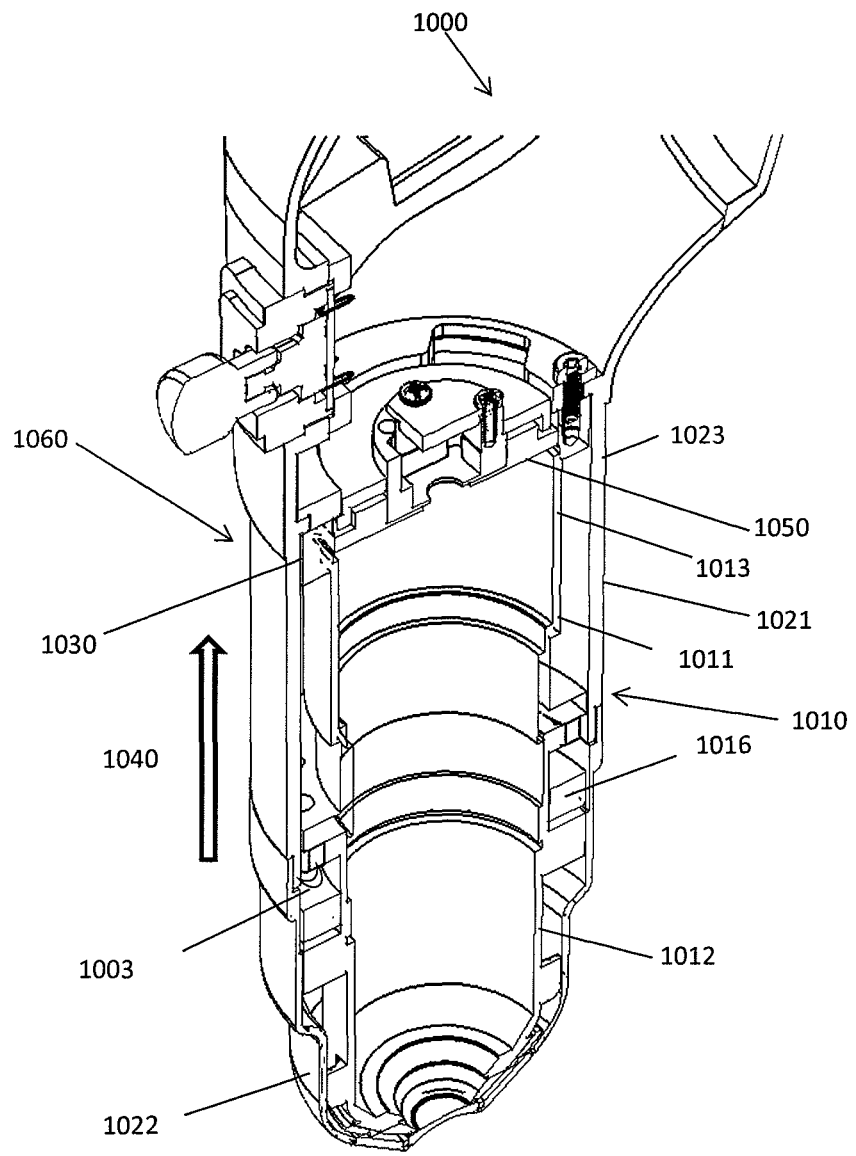
FIG. 10 schematically illustrates an eye imaging apparatus comprising a heat dissipation module comprising a double shell structure according to various embodiments.

FIG. 10 schematically illustrates an eye imaging apparatus 1000 comprising a heat dissipation module 1060 comprising a double shell structure 1010 according to various embodiments. The high power light sources 1003, for example, the light emitting elements, in the imaging apparatus 1000 can generate a lot of heat during the operation of the apparatus 1000. However, the temperature on the exterior surfaces of the apparatus 1000 can be required to be below certain levels. For example, the surface which comes in contact with the patient can be required to have a lower temperature than the surface where only the operator can touch. Because the light sources 1003, which can be mounted on the heat sink ring 1016, are located close to the portion of the imaging apparatus 1000 that contacts with the patient, a special double shell structure 1010 can used to direct the heat away from the patient. For example, the temperature of the front portion 1122 of the outer shell housing 1121 can be required to be less than 41 degree C. according to FDA regulations, and the temperature of the other portion of the housing can be required to be less than 48 degree C. according to FDA regulations.

The double shell structure 1010 can comprise an inner shell 1011 comprising a forward lens shell 1012 and a rearward lens shell 1013 and an outer shell 1021. The inner shell 1011 can be the portion of the shell which holds the optical lenses. In the double shell structure 1010, portions of the housing can comprise materials with good thermal conductivity and portions of the housing can comprise material with relatively poor thermal conductivity. For example, the inner shell 1011 can comprise material with good thermal conductivity, which can be used to conduct the heat. The inner shell 1011 can comprise materials with thermal conductivity higher than 10, 20, 40, 80, 100, or 200 $W \cdot m^{-1} \cdot K^{-1}$ or values therebetween. For example, the inner shell can comprise material, like aluminum alloy and brass, with good thermal conductivity, which can be used to conduct the heat. In various embodiments, the front portion 1022 of the outer shell 1021 of the housing of the apparatus 1000, which can be in contact with an eye of a patient, can comprise materials with relatively poor thermal conductivity, like Titanium alloy or stainless steel, to protect the patient; the back portion 1023 of the outer shell 1021 of the housing, which can only be touched by the operator, can comprise materials with good thermal conductivity, like aluminum alloy. The back portion 1023 of the outer shell 1021 of the housing can be used as the heat dissipation surface to release the heat, through both convection and radiation. The inner shell 1011 comprising the forward lens shell portion 1012 and the rearward lens shell portion 1013 can conduct the heat, from the light sources 1003, away from the front portion 1022 of the outer shell 1021 and to the back portion 1023 of the outer shell 1021 through a specially designed thermal conductive joint surface 1030. The arrow 1040 illustrates the direction of heat flow. In some embodiments, the light source 1003 can be embedded in the heat sink 1016. In various embodiments, a portion of the heat sink is disposed directly in front of the light source 1003 to receive heat radiated therefrom and conduct that heat away. The heat generated by the light source 1003, can be transferred to the heat sink 1016, then to the forward lens shell portion 1012. To prevent high temperatures for some of temperature sensitive electronics, the structure 1050 which supports those electronics can comprise a thermally insulated material, like Nylon.

Figure 11:
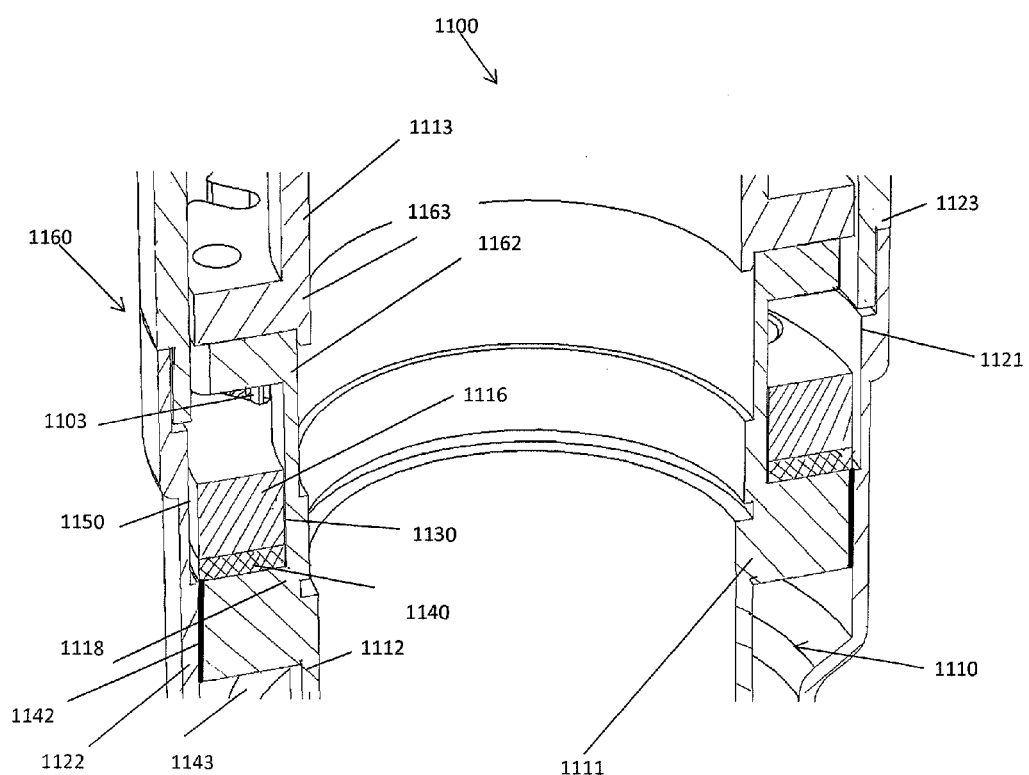
FIG. 11 further illustrates the detailed example configuration of the heat dissipation module of the imaging apparatus according to various embodiments of the invention.

FIG. 11 further illustrates the detailed configuration of the double shell structure 1110 of the heat dissipation module 1160 of the imaging apparatus 1100 according to various embodiments. As discussed above, the inner 1111 shell can comprise a forward lens shell 1112 and a rearward lens shell 1113. The light source 1103 can be mounted onto the heat sink 1116 comprising a ring to increase the mass of the heat sink 1116, thus increasing heat dissipation capability. The heat generated by the light source can be first transferred to the heat sink 1116. The heat sink 1116 can comprise material with thermal conductivity higher than 10, 20, 40, 80, 100, or 200 $W \cdot m^{-1} \cdot K^{-1}$ or values therebetween. For example, the heat sink 1116 can comprise material with good thermal conductivity, like brass or copper. A layer of thermally conductive grease 1130 can be used to help transfer the heat from the heat sink 1116 to the forward lens shell 1112. The forward lens shell 1112 can be configured with narrow cross-section 1118 toward the frontal portion of the inner shell 1111, in order to further reduce the transfer of energy forward. A thermal insulating ring 1140 comprising thermally insulated material can be inserted under the heat sink 1116 to reduce the direct heat transfer from the heat sink 1116 to the portion of the forward lens shell 1112 below the narrow cross-section 1118. A thermal insulation shim 1142 can also be inserted between the forward lens shell 1112 and the front portion 1122 of the outer shell housing 1121. A low thermal conductive material 1143 can be further inserted between the forward lens shell 1112 and the front portion 1122 of the outer shell housing 1121. An air gap 1150 can be maintained between the heat sink 1116 and the front portion 1122 of the outer shell housing 1121 to prevent direct heat transfer. The gap 1150 can also be filled with thermally insulating material or a shim with thermally insulating material. The heat collected in the forward lens shell 1112 is transferred to the rearward lens shell 1113 through their large mating flanges 1162 and 1163, which can comprise highly thermal conductive material. Although a portion of the heat can be leaked into the back portion 1123 of the outer shell 1121, and heat up the surface of the outer shell 1121, the operator may not feel the heat because the surface is covered by the handgrip comprising thermally insulated material. Eventually, the majority of the heat is transferred to the back portion 1123 of the outer shell 1121 while a large surface is created to disperse the energy, where the front portion 1122 of the outer shell housing 1121 are kept cool. For example, the temperature of the front portion 1122 of the outer shell housing 1121 is less than 35 degree C., 39 degree C., 40 degree C., 41 degree C. or any other value that complies with relevant regulations, and the temperature of the other portion of the housing is less than 45 degree C., 46 degree C., 48 degree C., or any other value that complies with relevant regulations.

There are many variations of the double shell structure 1110. In some other embodiments, the double shell structure can be a partial double shell structure. For example, the front portion of the housing can comprise an inner shell and an outer shell, while the back portion of the housing is a one piece single shell. Additionally, in some embodiments, the system is not designed for the user to repeatedly detach the front module from the main module and instead of using separate the front and rear inner shells, an inner shell having front and rear portions may be employed. An inner shell having a front portion and a rear portion rather that detachable front and rear shells may also be used for other purposes in different embodiments. Additionally, in some embodiments the optical sensor may be in the front portion (or the front shell) together with imaging optics and/or the light sources may be in the rear portion (or the rear shell) and, for example, fibers may be used to convey the light to the front portion (or the front shell).

Figures 12A, 12B:
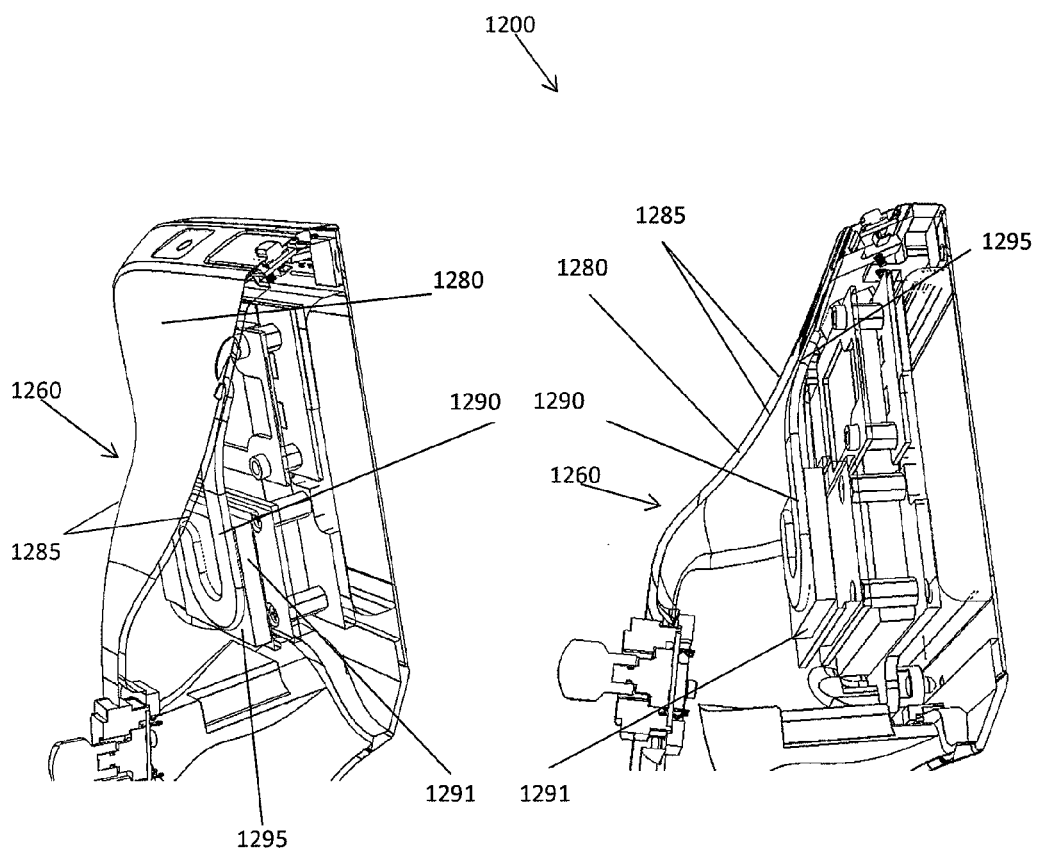
FIG. 12(A) schematically illustrates the heat dissipation module of the imaging apparatus comprising a heat pipe and a thermally conductive housing according to various embodiments.
FIG. 12(B) schematically illustrates the heat dissipation module of the imaging apparatus comprising a heat pipe and a thermally conductive housing viewed from another angle according to various embodiments.

FIG. 12(A) and FIG. 12(B) schematically illustrate the heat dissipation module 1260 of the imaging apparatus 1200 comprising a heat pipe 1290 and a thermally conductive housing 1280 viewed from two different angles according to various embodiments of the invention. The imaging apparatus 1200 can be configured to be watertight without an exhaust air duct for safety. However, the electronic devices 1291 in the imaging apparatus 1200 generate a large amount of heat during the operation, which has to be dispersed through the housing 1280 of the imaging apparatus 1200. The housing 1280 of the imaging apparatus 1200, or at least portion of the housing 1280, can comprise a large heat dissipation surface comprising thermally conductive material(s), for example aluminum alloy. The electronic devices 1291, which are also the major heat sources, can be positioned inside the housing 1280. To efficiently transfer the heat from the electronic devices 1291, which is the heat source, to the housing 1280, the large heat disperse surface, a heat pipe 1290 can be used.

The heat pipe 1290 can comprise a hollow tube comprising copper, aluminum or other material. A liquid state of a working fluid can be disposed in the hollow tube 1290. The heat pipe 1290 is a heat-transfer device that combines the principles of both thermal conductivity and phase transition to efficiently manage the transfer of heat between two solid interfaces, the electronic devices 1291 and the housing 1280. The two ends of the heat pipe 1290 can be mounted to the solid surfaces, for example, the surfaces of the electronic devices 1291 and the housing 1280. The surfaces of the electronic devices 1291 and the housing 1280 can have a thermally conductive layer or a thermally conductive adhesive 1295 disposed thereon. The thermally conductive layer or a thermally conductive adhesive 1295 can often be electrically insulated material(s). At the hot interface of the heat pipe 1290, the liquid state of the working fluid in the tube turns into a vapor by absorbing heat from the hot solid surface, for example, the surface of the electronic devices 1291. The vapor then travels along the heat pipe 1290 to the cold interface at another end, for example, the surface of the housing 1280, and condenses back into a liquid—releasing the latent heat. The liquid then returns to the hot interface, for example, the surface of the electronic devices 1291, through capillary action, centrifugal force, or gravity, and the cycle repeats. The working fluid can often comprise ammonia, alcohol (methanol), ethanol or other material. FIG. 12 schematically demonstrates the configuration in which the heat generated by an electronic device 1291, for example, a wireless transmitter, is transferred to the thermally conductive housing of the imaging apparatus 1200 to achieve efficient cooling. Other electronic devices inside the housing 1280 can also be cooled with small heat pipes in order to reduce the overall temperature in the imaging apparatus 1200.

In various embodiments, the heat dissipation module 1260 of the imaging apparatus 1200 can further comprise special coatings or specially treated surfaces 1285 for an inside surface and/or an outside surface of the housing 1280. To further reduce the temperature of the housing 1280 of the imaging apparatus 1200, the housing 1280 can comprise special coatings or specially treated surfaces 1285 on the inside surface, or the outside surface, or both the inside surface and the outside surfaces. To enhance the heat dissipation through radiation, the surfaces of the housing 1280 can be configured to be not only heat conductive, but also with high optical emissivity. The special coatings or treated surfaces 1285, although can have different colors, exhibit high emissivity larger than 0.3, 0.4, 0.5, 0.7, 0.9, or 1.0. The coatings or the surfaces 1285 with high emissivity can be efficient in absorbing the thermal radiation and radiating the heat out into space (e.g., ambient). Accordingly, in some embodiments, the housing 1280 of the imaging apparatus 1200 can have special coatings or specially treated surfaces 1285 disposed thereon. In some other embodiments, the portion of the housing 1280 which houses the cuboid portion of the imaging apparatus 1200 can have special coatings or specially treated surfaces 1285 disposed thereon with high absorption in the optical wavelength from 4 microns to 40 microns. In some embodiments, for example, the housing 1280 of the imaging apparatus 1200 can have specially treated surfaces 1285 through special surface blacking process. In some other embodiments, the housing 1280 of the imaging apparatus 1200 can have special coatings with thin, but high emissivity material, for example, an infrared absorbing paint with high absorption closed to that of a black body in the optical wavelength from 4 microns to 40 microns.

FIG. 13(A) and FIG. 13(B) schematically illustrate a perspective view and a side view of an eye imaging apparatus 1300 comprising an interconnect locking structure 1333, which includes in part a locking ring 1303 according to various embodiments. The eye imaging apparatus 1300 can comprise a front imaging module 1301 and a main module 1302. The front imaging module 1301 can be configured to be repeatedly attached to and removed from the main module 1302. The front imaging module 1301 may be disposed at the front portion 1316 of the cylindrical portion 1311 of the housing. The main module 1302 may be disposed at the back portion 1318 of the cylindrical portion 1311 and in the cuboid portion 1312 of the housing. The eye imaging apparatus 1300 may be used to image the posterior segment of the eye through the front imaging module 1301. The front imaging module 1301 may be removable and replaced with other imaging and illumination optics in various embodiments. When imaging and illumination optics are capable of being removed or replaced, the potential applications of the eye imaging apparatus 1300 may be significantly expanded. For example, the eye imaging apparatus 1300 may be used to image the posterior segment of the eye with various magnifications and under different illumination conditions, including illumination from broadband and/or narrowband light sources. The iris of the patient may or may not need to be dilated with special drugs prior to the imaging procedure. Color images from the posterior segment of the eye may also be obtained in the form of mono (2D) or stereoscopic (3D) images. The front imaging module 1301 may be designed to image the anterior segment of the eye as well.

The interconnect locking structure 1333, which includes in part the locking ring 1303 as well as part of the front imaging module 1301 and main imaging module 1302 facilitates convenient attachment and removal of the front imaging module 1301 with respect to the main module 1302. As illustrated, the cuboid portion 1312 can be mounted on top of the cylindrical portion 1311 at an inclined angle, for allowing easier operation of the apparatus 1300 by the operators. The locking ring 1303 as part of the interconnect locking structure 1333 can be configured to attach and/or remove the front imaging module 1301 from the main module 1302. For example, the removable front imaging module 1301 may be detached from the main module 1302 by moving or rotating the locking ring 1303 from a locked position to an unlocked position. The use of the locking ring 1303 may not only prevent accidental removal of the removable front imaging module 1301, but also may seal the gaps between the removable front imaging module 1301 and a main module 1302 when a water-tight seal is desired. The locking structure can be employed to allow the operators to both securely attach the front imaging module 1301 with the main module 1302, and to detach the front imaging module 1301 from the main module 1302. Part of the locking structure 1333 can be disposed in the front imaging module 1301, and part of the locking structure can be disposed in the main module 1302. In various embodiments, a liquid-tight sealing structure can be formed from two circular ring shaped surfaces that can be disposed within or under the locking ring 1303 and around the cylindrical portion 1311 of the eye imaging apparatus 1300. The two ring shaped surfaces, which can be disposed in the front imaging module 1301 and the main module 1302, respectively, can be brought to contact each other. In various embodiments, these two ring shaped surfaces can have precisely matched contact surfaces to facilitate mating therebetween. The two ring shaped surfaces may comprise metal, plastic, rubber materials or other materials. When the two ring-shaped surfaces are pressed against each other, a liquid-tight seal can be formed to prevent water or liquid from entering the cylindrical portion 1311 of the housing from the outside. After the front imaging module 1301 is attached to the main module 1302, the locking ring 1303 may be moved or rotated to the locked position from the unlocked position. The requirement of moving the locking ring 1303 to the locked position may help to prevent accidental removal of the front imaging module 1301 and enable the liquid-tight sealing between the front imaging module 1301 and the main module 1302.

FIG. 14 schematically illustrates an imaging apparatus 1400 comprising an interconnect locking structure 1433 according to various embodiments. The interconnect locking structure 1433 comprises a locking ring 1403 and a plurality of mechanical interlocking tracks. The interconnect locking structure 1433 can be disposed outside an optical path 1440 of the imaging optics. The interconnect locking structure 1433 can be disposed on the cylindrical portion 1411 with an inner diameter larger than 10 mm, 15 mm, 20 mm, 30 mm, or 40 mm but may have a diameter ranging between any of these values. A first portion 1433A of the interconnect locking structure 1433 can be disposed within the front imaging module 1401 and a second portion 1433B of the interconnect locking structure 1433 can be disposed within the main module 1402.

In various embodiments, the interconnect locking structure 1433 can be configured to enable repeatedly remove the front imaging module 1401 from the main module 1402 and attach the front imaging module 1401 to the main module 1402, thus allowing the operator to switch among the multiple imaging optics available for multiple imaging modalities during the imaging sessions. The locking ring 1403 can be configured to securely lock the front imaging module 1401 with the second portion 1433B of the interconnect locking structure 1433. Therefore, the front imaging module 1401 can be securely locked with the main module 1402 to prevent accidental detachment of the front imaging module 1401 from the main module 1402 during the imaging session. In some embodiments, when the lock ring 1403 is pushed upward along the cylindrical portion 1411, the front imaging module 1401 is unlocked and free to be twisted and detached from the main module 1402 of the imaging apparatus 1400. In some other embodiments, when the lock ring 1403 is pushed downward along the cylindrical portion 1411, the front imaging module 1401 is unlocked and free to be twisted and detached from the main module 1402 of the imaging apparatus 1400. In some alternative embodiments, the removable front imaging module is detached from the main module by rotating the locking ring from a locked position to an unlocked position. Another front imaging module 1401 can be inserted into the second portion 1433B of the interconnect locking structure 1433 and twisted in the opposite direction which in turn gradually pulls the front imaging module 1401 and the main module 1402 together through the plurality of mechanical interlocking tracks disposed in the interconnect locking structure 1433. The rotation of the front imaging module 1401 can be stopped when the front imaging module 1401 reaches an end point, at which a locking mechanism can automatically click in and lock the front imaging module 1401 to prevent the front imaging module 1401 from any further rotation.

Figures 15A, 15B:
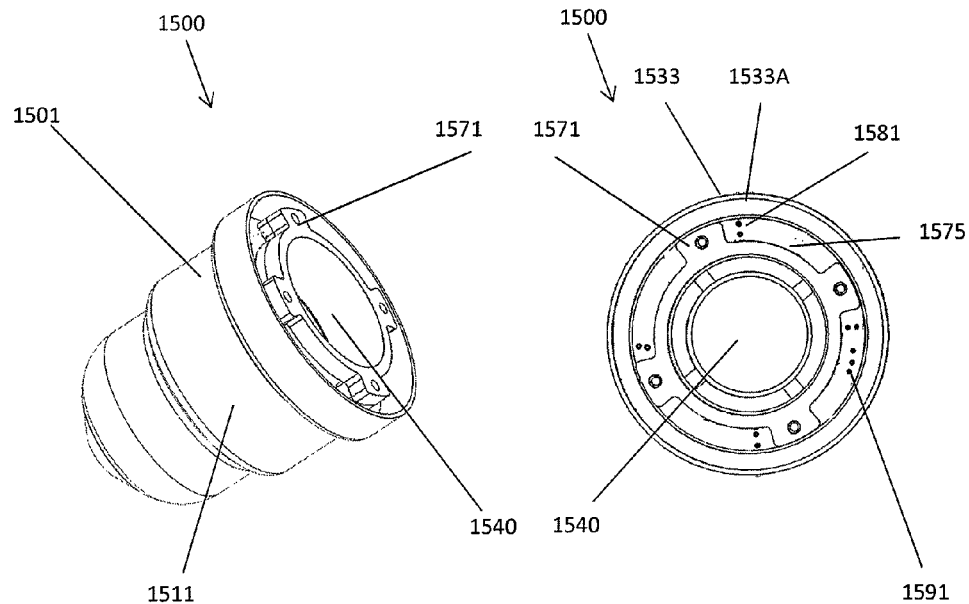
FIG. 15(A) schematically illustrates a perspective view of a first portion of the interconnect locking structure within the front imaging module of the imaging apparatus according to various embodiments.
FIG. 15(B) schematically illustrates a top view of the first portion of the interconnect locking structure within the front imaging module of the imaging apparatus according to various embodiments.
Figures 15C, 15D:
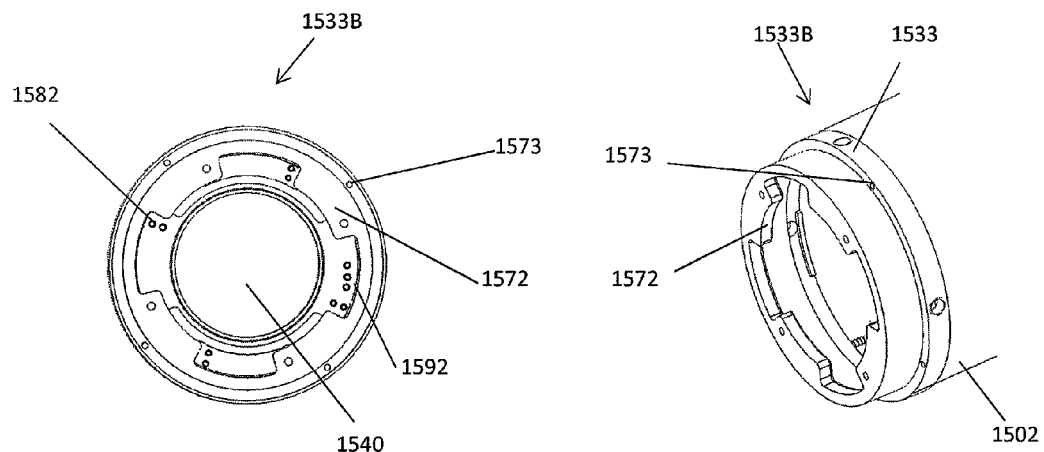
FIG. 15(C) schematically illustrates a top view of a second portion of the interconnect locking structure within main module of the imaging apparatus according to various embodiments.
FIG. 15(D) schematically illustrates a perspective view of the second portion of the interconnect locking structure within the main module of the imaging apparatus according to various embodiments.

FIG. 15(A) and FIG. 15(B) schematically illustrate a perspective view and a rear view of the first portion 1533A of the interconnect locking structure 1533 within the front imaging module 1501 of the imaging apparatus 1500 according to various embodiments. FIG. 15(C) and FIG. 15(D) schematically illustrate a front view and a perspective view of the second portion 1533B of the interconnect locking structure 1533 within the main module 1502 according to various embodiments. Referring to FIG. 15(A), FIG. 15(B), FIG. 15(C) and FIG. 15(D), the interconnect locking structure 1533 can comprise a locking structure comprising a plurality of counterpart pairs of interconnect flanges 1571 and 1572, and a plurality of locking pins 1573 and receiving holes, disposed in the front imaging module 1501 and the main module 1502. The interconnect locking structure 1533 can be positioned outside the optical path 1540 of the imaging optics. The front imaging module 1501 can be clenched together with the main module 1502 through the plurality of mating pairs of interconnect flanges 1571 and 1572 disposed in both the front imaging module 1501 and the main module 1502. For example, the interconnect locking structure 1533 can further comprise a plurality of compression springs in some embodiments. Each of the plurality of compression springs can be disposed outside each of the plurality of locking pins 1573. The plurality of compression springs can force the plurality of locking pins 1573 in a down position. When the new front imaging module 1501 is inserted into the interconnect locking structure 1533, is rotated, and reaches the end point of the track, the receiving holes in the front module 1501 will be aligned with the locking pins 1573. Then the compression springs can push the locking pins 1573 to the locking positions, thus locking the front module 1501 with the main module 1502. The locking ring can be used to withdraw the pins from the locking position to disengage the front module 1501 from the main module 1502.

The flanges 1571 and 1572 not only act as mechanical components, but also as thermal conductive elements. When matched together, the flanges 1571 and 1572 can transfer the heat generated by the light source in the front imaging module 1501 through tightly clenched surfaces to the rearward lens shell of the inner shell and dissipated to the outer shell housing. In some embodiments, at least 2 pairs of interconnect flanges 1571 and 1572 can be used to connect the front imaging module 1501 and the main module of the imaging apparatus 1500 and transfer the heat from the front imaging module 1501 to the outer housing; at least 2 locking pins 1573 can be used to lock the flanges 1571 and 1572 into the locking positions.

In some embodiments, the light sources of the imaging apparatus 1500 can be disposed in the front imaging module 1501. In order to supply the light sources with electrical power, the interconnect locking structure 1533 can further comprise a plurality of electrically conductive power contacts 1582 and counterpart or matching electrical power contacts 1581. The electrically conductive power contacts 1582 can be configured to be retractable. The electrically conductive power contacts 1582, for example, can comprise electrically conductive pins made of, for example gold coated brass. The electrically conductive power contacts 1582 can be disposed in the second portion 1533B of the interconnect locking structure 1533 in the main module 1502. The front imaging module 1501 can comprise an electrically insulated flange 1575. The matching or counterpart electrical power contacts 1581 can be disposed in the electrically insulated flange 1575 in the first portion 1533A of the interconnect locking structure 1533 in the front imaging module 1501. The electrical power contacts 1581 in the front imaging module 1501 can be connected with the light sources located in the front imaging module 1501. In some alternative embodiments, electrically conductive power contacts 1582 that are retractable can be disposed in the electrically insulated flange 1575 in the first portion 1533A of the interconnect locking structure 1533 in the front imaging module 1501, and the matching electrical power contacts 1581 can be disposed in the second portion 1533B of the interconnect locking structure 1533 in the main module 1502. The imaging apparatus 1500 comprise at least two pairs of electrically conductive power contacts 1581 and 1582. The number of pairs could be 4, 5, 7, 8 and even more.

In various embodiments, the imaging apparatus 1500 can further comprise a plurality of electrical signal contacts 1592 on the main module and matching or counterpart electrical signal contacts 1591 on the front module. In some embodiments, in order to control the light sources and allow the imaging apparatus 1500 to identify the different front imaging modules 1501 inserted into the second portion 1533B of the interconnect locking structure 1533, the interconnect locking structure 1533 can comprises the plurality of electrical signal contacts 1592. The electrical signal contacts 1592 can be configured to be retractable. The electrical signal contacts 1592, for example, can comprise electrically conductive pins. The electrical signal contacts 1592 can be disposed in the second portion 1533B of the interconnect locking structure 1533 in the main module 1502. The matching or counterpart electrical signal contacts 1581 can be disposed in the electrically insulated flange 1575 in the first portion 1533A of the interconnect locking structure 1533 in the front imaging module 1501. The electrical signal contacts 1592 and matching electrical signal contacts 1591 can provide control signals for the electronics, for example, associated with the light source in the front imaging module 1501. The retractable electrical signal contacts 1592 and the matching electrical signal contacts 1591 can also send identification number (ID) of the front imaging module 1501 back to the main module 1502. In some alternative embodiments, electrical signal contacts 1592 that are retractable can be disposed in the first portion 1533A of the interconnect locking structure 1533 in the front imaging module 1501; the matching electrical signal contacts 1591 can be disposed in the second portion 1533B of the interconnect locking structure 1533 in the main module 1502. As the front imaging module 1501 is inserted into the interconnect locking structure 1533 and securely locked, proper electrical contacts can be made between the retractable electrical signal contacts 1592 and the matching electrical signal contacts 1591, and result in reliable electrical conduction for current. The imaging apparatus 1500 comprise at least two pairs of electrically conductive signal contacts 1591 and 1592. The number of pairs could be 4, 5, 7, 8 and even more.

Figure 16A:
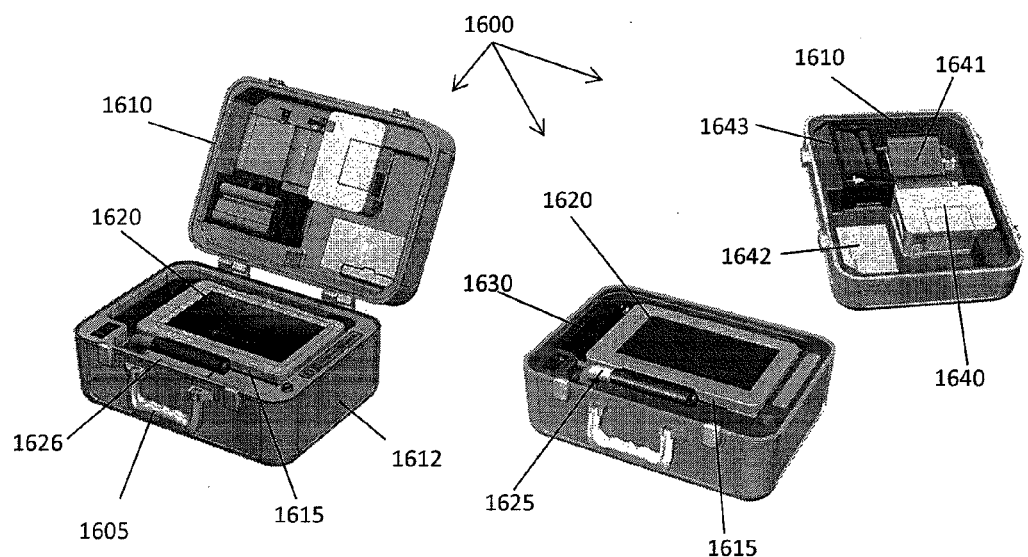
FIG. 16(A) schematically illustrates a carrying case comprising a flat panel display for the eye imaging apparatus according to various embodiments.
Figure 16B:
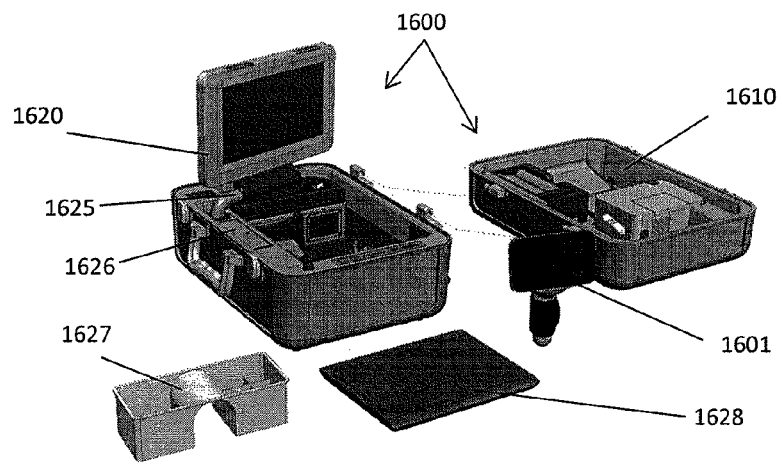
FIG. 16(B) schematically illustrates the carrying case when the flat panel display is in a working position according to various embodiments.

FIG. 16(A) and FIG. 16(B) schematically illustrate a carrying case 1600 for the eye imaging apparatus 1601 according to various embodiments. The eye imaging apparatus may be carried in a small carrying case 1600 with a handle 1615 because the eye imaging apparatus is relatively compact and easy to carry. For example, in some embodiments, a carrying case can have dimensions less than about 600 mm×400 mm×300 mm and can weigh less than about 20 kg. In some embodiments, for example, the carrying case (with or without the handheld device inside) can be between (600 mm and 300 mm)×(400 mm and 200 mm)×(300 and 150 mm). Similarly, in some embodiments the carrying case can have a volume less than 72,000 cm$^3$. In some embodiments the carrying case can have a volume between 72,000 cm$^3$ and 9000 cm$^3$. Also, the carrying case 1205 can weigh between about 10 kg and about 20 kg in some embodiments, or between about 5 kg and about 20 kg, in some embodiments. Sizes outside these ranges for the carrying case 1600 are also possible.

Referring to FIG. 16(A) and FIG. 16(B), the carrying case 1600 can have a main portion 1612 having an open inner region for storage, a cover 1610 and a handle 1605. The carrying case 1600 can have at least one of a display monitor 1620, a printer 1640, or a charging station 1680 attached to the carrying case 1600. In some embodiments, the carrying case 1600 can have at least one of a display monitor 1620, a printer 1640, or a charging station 1680 integrated to the carrying case 1600. The display monitor 1620 and printer 1640 can be configured to receive images from the eye imaging apparatus 1601. The charging station 1680 can be configured to charge the eye imaging apparatus 1601. The carrying case 1600 can be configured to house the eye imaging apparatus 1601 as well as a computing module 1615, the display monitor 1620, a wireless keyboard 1628, a removable electronic data storage unit 1626, a DC converter and power cord 1630 for the main portion 1612 and a storage container 1627 in various embodiments. In some embodiments, the carrying case can further comprise the picture printer 1640, a cartridge for printer paper 1641, printer papers 1642, a DC converter and power cord 1643 for the printer 1640. In some embodiments, the display monitor 1620 and the computing module 1615 can be integrated to be one unit as shown in FIG. 16(A) and FIG. 16(B). In some other embodiments, the computing module 1615 can be separated from the display monitor 1620, and be placed in a different location than the display monitor 1620 in the carrying case 1600. In some embodiments, display monitor 1620 can have a touch screen function. In some embodiments, the removable electronic data storage unit 1626 can be a custom-built hard disk drive, which can be removable such that the removable electronic data storage unit 1626 can be taken out to be placed in a secure location for data safety. In case the carrying case 1600 is damaged or lost, the data is still saved. The carrying case 1600 can be transported for example by lifting with a handle 1605 or with a suitcase dolly.

In various embodiments, the imaging apparatus 1601 can be used in an eye imaging medical system. The computing module 1615 can be configured to receive data input via for example the wireless keyboard 1628 as well as images from the eye imaging apparatus 1601, the display monitor 1620 can be used to display and review the patients' images, and the picture printer 1640 can be used to print both the report and the images of the eyes of the patients.

In some embodiments, the carrying case 1600 is configured to have a removable cover 1610 holding the picture printer 1640. FIGS. 16(A) and 16(B) show the removable cover 1610 and the main portion 1612 of the carrying case 1600 to which the removable cover 1610 is removably attached. Hinges that connect the cover 1610 to the main portion 1612 of the carrying case can be configured to permit quick and convenient detachment and reattachment of the cover without the use of tools. Accordingly, the removable cover 1610 can be conveniently separated and placed in a different location than the carrying case 1600. The removable cover 1610 can enable the imaging apparatus 1601 and the supporting electronics to be placed closer to the patient and the picture printer 1640 to be placed at a distance from the patient. At the same, the user can carry just one case 1600 with all of the necessities placed therein. The removable cover 1640 can be conveniently reattached to the main portion of the carrying case.

In order to reduce or minimize the overall volume of the carrying case 1600, all of the components inside the carrying case 1600 are packed closely and placed in a careful arrangement. The carrying case 1600 can have internal surfaces contoured to compactly fit the different components. Cushioning or other surfaces that protect the components within the carrying case from damage may also be included. Some of the components can be integrated with the carrying case 1600, for example, enclosed behind panels of the carrying case 1600. In some embodiments, the display monitor 1620 can be mounted on a multi-axis stand 1625, which allows the display monitor 1620 to be rotated in a first direction and a second direction, which will be discussed in detail below in FIG. 16(D). During the transportation, the display monitor 1620 can be folded down and locked in a folded storage position with the help of the multi-axis stand 1625 and other external locking mechanism as shown in FIG. 16(A). Before the eye examination, the display 1620 can be raised to a working position, which allows users to take out the wireless keyboard 1628, the storage container 1627, and the imaging apparatus 1601 one by one as shown in FIG. 16(B).

In some embodiments, the imaging apparatus 1601, the computing module 1615 and the picture printer 1640 can be powered by separated energy sources. The imaging apparatus 1601 and the computing module 1615 can also have internal batteries. The computing module 1615, which can be placed in the main portion of the carrying case 1600, and the picture printer 1640, which can be placed in the removable cover 1610, can be powered by external AC power supplies by plugging in their respecting power cords 1630 into the AC power outlets. The computing module 1615 and the imaging apparatus 1601 can also be powered by their internal battery respectively. In some other embodiments, the picture printer 1640 can also have an internal battery for working without the external power.

Figure 16C:
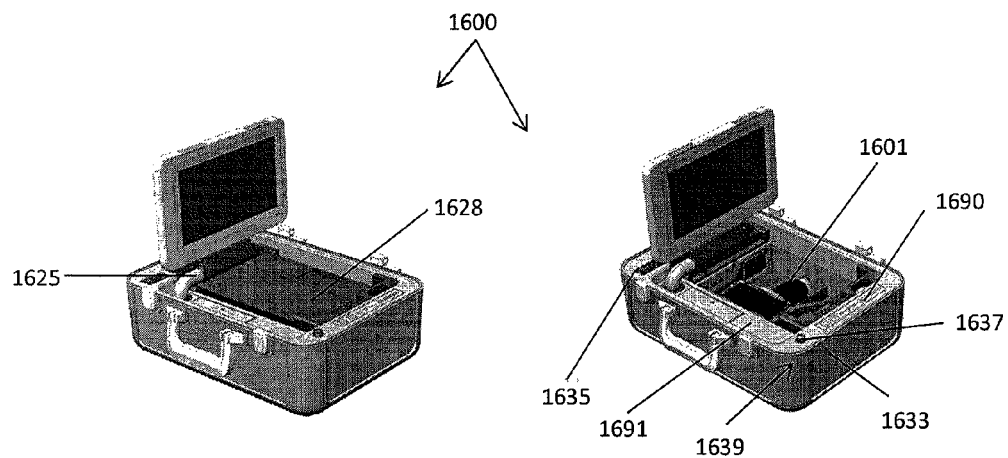
FIG. 16(C) schematically illustrates the carrying case further comprising an electronic system wherein the electronic system comprises a computing module, a power entry module, a power on/off switch and a communication module.

FIG. 16(C) schematically illustrates the carrying case 1600 further comprising an electronic system 1639 according to various embodiments. The electronic system 1639 can comprise the computing module 1615, the display monitor 1620, a power entry module 1635, a power on/off switch 1637 on a control panel 1690, a communication module 1633 underneath the control panel 1690 and a plurality of wires. The electronic system 1639 can be integrated with the carrying case 1600. The plurality of wires can be placed inside the stand 1625, or underneath the control panel 1690, and/or in an enclosed compartment 1691 of the carrying case 1600. To power up the electronic system 1639 by AC source, the power cord 1630 can be first plugged into the power entry module 1635 in one end, and plugged into the AC power outlet in another end. By pushing down the power on/off switch 1637, the whole electronic system 1639 in the carrying case 1600 can be powered up, including the computing module 1615 and the communication module 1633.

Referring to FIG. 16(A) to FIG. 16(C), after computing module 1615, the picture printer 1640 and the imaging apparatus 1601 are powered up, the computing module 1615 will be automatically connected with the imaging apparatus 1601 and picture printer 1640 through wireless communication channels. The images captured by the imaging apparatus 1601 can be sent to the computing module 1615 in the carrying case 1600 and displayed on the display monitor 1620 in real time, while the same images can also be stored in the electronic data storage unit 1625, and printed out by the picture printer 1640. The electronic data storage unit 1625, which stores all of the patient information and pictures, can be removed from the carrying case 1600 and placed in a safe location. When the electronic system 1639 is powered up, the communication module 1633 can also automatically connect with local area computer network or internet wirelessly. Such connection enables the data exchanges between the electronic data storage unit 1625 and data storages connected with the local area computer network or internet. By pushing down the power on/off switch 1637 again, the whole electronic system 1639 in the carrying case 1600 can be shut down automatically.

Figure 16D:
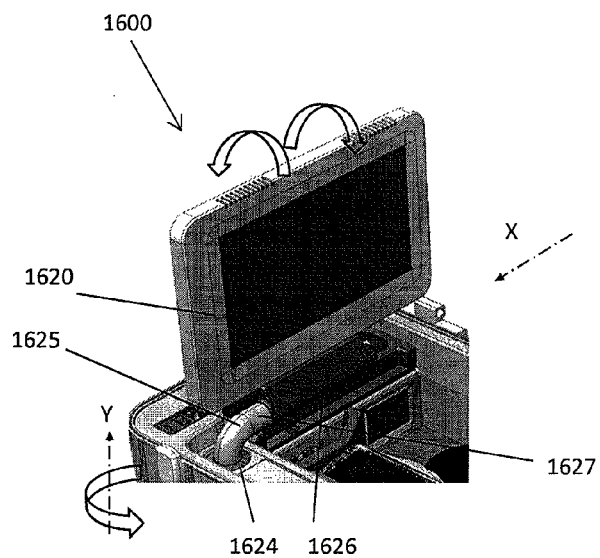
FIG. 16(D) schematically illustrates the multi-axis stand 1625 of the flat panel display 1620 according to various embodiments FIG. 16(E) schematically illustrates the carrying case further comprising an electrical recharging station according to various embodiments.

FIG. 16(D) schematically illustrates the multi-axis stand 1625 of the flat panel display 1620 according to various embodiments. In some embodiments, the multi-axis stand 1625 can comprise a hollow tube 1627 that is bent, for example, at the middle. The multi-axis stand 1625 can comprise two rotational joints 1624 and 1626, which allow the display 1620 to be rotated in a first direction about the X-axis and a second direction about the Y-axis respectively. The electrical wires can be placed safely inside the hollow tube 1627 without been seen by users. The wires not only supply power to the display 1620, but also provide a wired communication channel between the display 1620 and the rest of the electronic system 1639. In some other embodiments, the multi-axis stand 1625 can comprise at least two hollow metal tubes and at least two rotational joints. The multi joint construction allows the users to swing the display in horizontal direction and tilt the display in vertical direction for better viewing experience. In some embodiments, only one joint and/or one direction of tilt more or less vertical or rotation left and right are provided.

Figure 16E:
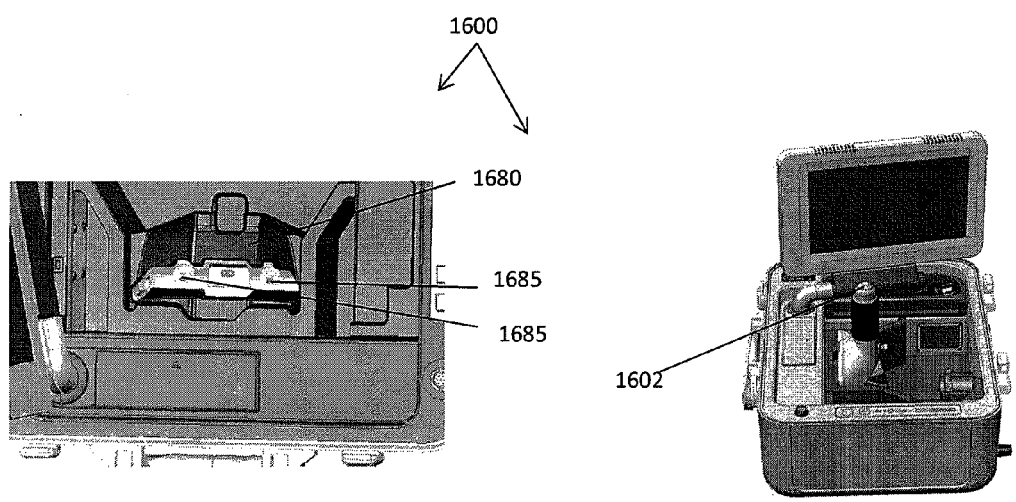

FIG. 16(E) schematically illustrates the carrying case 1600 comprising an electrical recharging station 1680 according to various embodiments. In various embodiments, the electrical recharging station 1680 allows the users to recharge the imaging apparatus 1601 during and/or after the imaging session. The electrical recharging station 1680 can comprise a plurality of retractable electrical contacts 1685. Through the power ports built into the housing of the imaging apparatus 1601 and corresponding retractable electrical contacts 1685 in the electrical recharging station 1680, the battery in the imaging apparatus 1601 can be recharged. When the imaging apparatus 1601 is plugged into the re-charging station 1680 with a front end 1602, which can be in contact with the patient's eye, pointing upward, the station 1680 also provides a safe and secured resting station for the imaging apparatus 1601 when it is not used for photographing the patients. Such arrangement also prevents the font end 1602, the patient contacting area to be touched accidentally by the users or foreign objects.

While the present invention has been disclosed in example embodiments, those of ordinary skill in the art will recognize and appreciate that many additions, deletions and modifications to the disclosed embodiment and its variations may be implemented without departing from the scope of the invention.

A wide range of variations to those implementation and embodiments described herein are possible. Components and/or features may be added, removed, rearranged, or combinations thereof. Similarly, method steps may be added, removed, and/or reordered.

Likewise various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Accordingly, reference herein to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below.

Additionally s used herein, a phrase referring to "at least one of" a list of items refers to any combination of those items, including single members. As an example, "at least one of: a, b, or c" is intended to cover: a, b, c, a-b, a-c, b-c, and a-b-c.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be described as occurring in a particular order, this should not be understood as requiring that such operations be performed in the particular order described or in sequential order, or that all described operations be performed, to achieve desirable results. Further, other operations that are not disclosed can be incorporated in the processes that are described herein. For example, one or more additional operations can be performed before, after, simultaneously, or between any of the disclosed operations. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single product or packaged into multiple products. Additionally, other embodiments are within the scope of the following claims. In some cases, the actions recited in the claims can be performed in a different order and still achieve desirable results.

What is claimed is:

1. A method to operate an eye imaging apparatus comprising:
   using three fingers including a middle finger, a ring finger and a pinky finger to hold a handgrip of an eye imaging apparatus;
   using a thumb to secure the eye imaging apparatus, wherein the eye imaging apparatus comprises an optical window with a concave front surface for receiving an eye;
   engaging a bump of the handgrip by a palm to align the eye imaging apparatus precisely during an imaging session;
   using the index finger to operate a multi directional button of the eye imaging apparatus, the multi directional button comprising a plurality of electrical switches and receiving input based on movements in a plurality of directions;
   adjusting an intensity of a light source and a focus of the eye imaging apparatus by pushing the multi-directional button in two orthogonal directions; and
   triggering an image sensor of the eye imaging apparatus by pushing the multi-directional button inwardly.

2. The method in claim 1, further comprising sliding the handgrip onto a cylindrical portion of the eye imaging apparatus.

3. The method in claim 1, further comprising rotating the handgrip to a locked position.

4. An eye imaging apparatus comprising:
   a housing;
   a display disposed in the housing;
   a light source disposed in the housing and configured to illuminate an eye;
   imaging optics disposed in the housing and configured to form an image of the eye comprising an optical window on a distal end of the housing, the optical window comprising a concave front surface for receiving the eye;
   an image sensor disposed in the housing and configured to receive said image of the eye; and
   a handgrip comprising a bump extending outward from an exterior surface of a substantially cylindrical portion of the housing proximal to the optical window, wherein the bump is shaped to substantially match with a contour of a palm of a hand of an operator holding the eye imaging apparatus and is oriented such that the optical window is disposed distal to the hand and the display is disposed proximal to the hand when the bump engages the palm of the hand, wherein a position of the bump is configured to be adjustable with respect to the imaging optics;
   wherein the housing comprises an inner shell comprising a forward lens shell portion and a rearward lens shell portion, and an outer shell comprising a front portion and a back portion, the front portion of the outer shell comprising materials with relatively low thermal conductivity, the back portion of the outer shell comprising materials with high thermal conductivity.

5. The eye imaging apparatus in claim 4, wherein the light source and the heat sink are disposed in thermal contact with an outer surface of the inner shell.

6. The eye imaging apparatus in claim 4, wherein an air gap is positioned between the heat sink and the front portion of the outer shell housing to reduce direct heat transfer.

7. The eye imaging apparatus in claim 4, wherein a thermal insulation material is positioned between the heat sink and the front portion of the outer shell housing to reduce direct heat transfer.

8. The eye imaging apparatus in claim 4, wherein a pair of large mating surfaces are positioned between the forward lens shell and the rearward lens shell.

9. An eye imaging apparatus comprising:
a housing;
a display disposed in the housing;
a light source disposed in the housing and configured to illuminate an eye;
imaging optics disposed in the housing and configured to form an image of the eye comprising an optical window on a distal end of the housing, the optical window comprising a concave front surface for receiving the eye;
a focusing lens and an actuator of the focusing lens configured to adjust a focus of imaging optics; and
an image sensor disposed in the housing and configured to receive said image of the eye;
a handgrip disposed between the optical window and the display, the handgrip comprising a hollow ring disposed on an exterior surface of a substantially cylindrical portion of the housing proximal to the optical window;
a bump disposed at a side of the hollow ring extending outwardly, the bump having a convex shape with a height between 5 mm and 40 mm, a width between 5 mm to 40 mm, and a length between 20 m to 150 mm, the bump configured to fill a volume between the hollow ring and a palm of a hand of an operator when the palm engages the bump, thereby allowing the operator to align imaging optics and the display precisely with the eye during an imaging session, wherein a position of the bump is configured to be adjustable with respect to the imaging optics; and
a multi-directional button disposed proximal to the bump and in close proximity to an index finger when the palm engages the bump for convenient actuation and precise optical alignment, the multi-directional button comprising a plurality of electrical switches connected to the light source, the actuator of the focusing lens and the image sensor, the multi-directional button configured to permit movements in a plurality of directions and receive input based on the movements, the multi-directional button configured to adjust an intensity of the light source and the focus of imaging optics by being pushed in two orthogonal directions, and to trigger the image sensor by being pushed inwardly.

10. The eye imaging apparatus in claim 9, wherein the hollow ring is removable and re-attachable.

11. The eye imaging apparatus in claim 9, wherein the handgrip is configured to be rotatable around a central axis of the handgrip.

12. The eye imaging apparatus in claim 9, wherein an inner diameter of the hollow ring is slightly smaller than an outer diameter of the substantially cylindrical portion.

13. The eye imaging apparatus in claim 9, wherein a position of the bump is adjustable by rotating the hollow ring around the substantially cylindrical portion to accommodate both a left-handed operator and a right-handed operator.

14. The eye imaging apparatus in claim 9, wherein the housing has a size less than 250 mm along the longest dimension.

15. The eye imaging apparatus in claim 9, wherein the multi-directional button is positioned in a central location on the substantial cylindrical portion and symmetrical to a left side and a right side, thereby allowing for both the right-handed operation and left-handed operation.

16. An eye imaging apparatus comprising:
a housing having an inner shell comprising a forward lens shell portion and a rearward lens shell portion, and an outer shell comprising a front portion and a back portion;
a removable front imaging module comprising;
a light source disposed in the housing and configured to illuminate an eye;
an optical window disposed on a distal end and comprising a concave front surface for receiving the eye;
a focusing lens and an actuator of the focusing lens configured to adjust a focus of imaging optics;
a main module comprising an image sensor configured to receive an image of the eye;
a multi-directional button disposed on the main module, the multi-directional button comprising a plurality of electrical switches connected to the light source, the actuator of the focusing lens and the image sensor, the multi-directional button configured to permit movements in a plurality of directions and receive input based on the movements, the multi-directional button configured to adjust an intensity of the light source and the focus of imaging optics by being pushed in two orthogonal directions, and to trigger the image sensor by being pushed inwardly; and
a display; and
an interconnect locking structure comprising:
a locking ring, and
a plurality of interconnect flanges configured to connect the front imaging module and the main module, wherein the interconnect locking structure further comprises a first plurality of retractable electrically conductive power contacts and a second plurality of counterpart electrical power contacts,
wherein the plurality of flanges are configured to transfer heat generated by the light source to the rearward lens shell of the inner shell and dissipated to the outer shell of the housing, wherein the interconnect locking structure is configured to enable repeated removal of the front imaging module from the main module and repeated re-attachment of the front imaging module to the main module, and a liquid-tight seal between the front imaging module and the main module.

17. An eye imaging apparatus comprising:
a housing having an inner shell comprising a forward lens shell portion and a rearward lens shell portion, and an outer shell comprising a front portion and a back portion;
a removable front imaging module comprising:
a light source disposed in the housing and configured to illuminate an eye;
an optical window disposed on a distal end and comprising a concave front surface for receiving the eye; and
a focusing lens and an actuator of the focusing lens configured to adjust a focus of imaging optics;
a main module comprising:
an image sensor configured to receive an image of the eye and
a display; and a handgrip disposed between the optical window and the display, the handgrip comprising a hollow ring disposed on an exterior surface of a substantially cylindrical portion of the housing, a bump disposed at a side of the hollow ring extending outwardly, the bump having a convex shape with a height between 5 mm and 40 mm, a width between 5 mm to 40 mm, and a length between 20 m to 150 mm, the bump configured to fill a volume between the hollow ring and a palm of a hand of an operator when the palm engages the bump, thereby allowing the operator to align imaging optics and the display precisely with the eye during an imaging session, an interconnect locking structure comprising:
  a locking ring, and
  a plurality of interconnect flanges configured to connect the front imaging module and the main module, wherein the interconnect locking structure further comprises a first plurality of retractable electrically conductive power contacts and a second plurality of counterpart electrical power contacts,
  wherein the plurality of flanges are configured to transfer heat generated by the light source to the rearward lens shell of the inner shell and dissipated to the outer shell of the housing, wherein the interconnect locking structure is configured to enable repeated removal of the front imaging module from the main module and repeated re-attachment of the front imaging module to the main module, and a liquid-tight seal between the front imaging module and the main module.

* * * * *